US009771617B2

(12) United States Patent
Dezso et al.

(10) Patent No.: US 9,771,617 B2
(45) Date of Patent: Sep. 26, 2017

(54) MICRORNA BIOMARKERS INDICATIVE OF ALZHEIMER'S DISEASE

(75) Inventors: Zoltan Dezso, Boston, MA (US); Pavan Kumar, Somerville, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 324 days.

(21) Appl. No.: 14/128,888

(22) PCT Filed: Jun. 26, 2012

(86) PCT No.: PCT/US2012/044202
§ 371 (c)(1),
(2), (4) Date: Apr. 24, 2014

(87) PCT Pub. No.: WO2013/003350
PCT Pub. Date: Jan. 3, 2013

(65) Prior Publication Data
US 2014/0378439 A1   Dec. 25, 2014

Related U.S. Application Data

(60) Provisional application No. 61/501,720, filed on Jun. 27, 2011.

(51) Int. Cl.
*C12Q 1/68*   (2006.01)
(52) U.S. Cl.
CPC ..... *C12Q 1/6883* (2013.01); *C12Q 2600/158* (2013.01); *C12Q 2600/178* (2013.01)
(58) Field of Classification Search
None
See application file for complete search history.

(56) References Cited

U.S. PATENT DOCUMENTS

| | | |
|---|---|---|
| 7,291,488 B2 | 11/2007 | Wolfe et al. |
| 7,662,561 B2 | 2/2010 | Godfrey et al. |
| 7,964,192 B1 | 6/2011 | Schenk |
| 8,414,893 B2 | 4/2013 | Biere-Citron et al. |
| 8,551,703 B2 | 10/2013 | Medrano et al. |
| 8,609,660 B2 | 12/2013 | Trabanco-Suarez et al. |
| 8,613,920 B2 | 12/2013 | Lieberburg et al. |
| 8,637,525 B2 | 1/2014 | Boy et al. |
| 8,648,017 B2 | 2/2014 | Umansky et al. |
| 8,778,334 B2 | 7/2014 | El-Agnaf et al. |
| 8,945,829 B2 | 2/2015 | Keutgen et al. |
| 8,999,341 B1 | 4/2015 | Clube |
| 9,119,846 B2 | 9/2015 | Zisapel et al. |
| 9,175,094 B2 | 11/2015 | Pfeifer et al. |
| 9,340,830 B2 | 5/2016 | Lipson et al. |
| 2010/0151480 A1* | 6/2010 | Taylor .............. G07F 17/3258 435/6.16 |

FOREIGN PATENT DOCUMENTS

| | | |
|---|---|---|
| CN | 101386848 A | 3/2009 |
| CN | 102597260 A | 7/2012 |
| JP | 2004-161636 | 10/2004 |
| JP | 2006-176503 | 6/2006 |
| WO | 2007044937 A2 | 4/2007 |
| WO | 2008147839 A1 | 12/2008 |
| WO | 2008153692 A2 | 12/2008 |
| WO | WO-2009-009457 A1 | 1/2009 |
| WO | WO 2009015357 | 1/2009 |
| WO | 2009025852 A2 | 2/2009 |
| WO | 2009036236 A1 | 3/2009 |
| WO | 2009143379 A2 | 11/2009 |
| WO | WO-2011-012691 A1 | 2/2011 |
| WO | 2011029903 A1 | 3/2011 |
| WO | WO 2004002402 | 1/2014 |

OTHER PUBLICATIONS

Cogswell, J. et al., Identification of miRNA Changes in Alzheimer's Disease Brain and CSF Yields Putative Biomarkers and Insights into Disease Pathways. Journal of Alzheimer's Disease, 2008, 14: 27-41.
Finder, V., Alzheimer's Disease: A General Introduction and Pathomechanism. Journal of Alzheimer's Disease, 2010, 22: S5-519.
Finnerty, J. et al., The miR-15/107 roup of MicroRNA Genes: Evolutionary Biology, Cellular Functions, and Roles in Human Diseases. Journal of Molecular Biology, 2010, 402: 491-509.
Hebert, S. et al., Alterations of the microRNA network cause neurodegenerative disease. Trends Neurosci, Cell Press., 2009, 32(4): 199-206.
Hollingworth, P. et al., Common variants at ABCA7, MS4A6A/MS4A4E, EPHA1, CD33 and CD2AP are associated with Alzheime's disease. Nature Genetics, 2011, 43 (5): 429-235.
International Preliminary Report on Patentability, PCT/US2012/044202, Jan. 7, 2014.
International Search Report, PCT/US2012/044202, Dec. 21, 2012.
Naj, A. et al., Common variants at MS4A4/MS4A6E, DC2AP, CD33 and EPHA1 are associated with late-onset Alzheimer's disease. Nature Genetics, 2011, 43 (5): 436-441.
Nelson, P. et al., MicroRNAs (miRNAs) in Neurodegenerative Diseases. Brain Pathol., 2008, 18: 130-138.
Nunez-Iglesias, J. et al., Joint Genome-Wide Profiling of miRNA and mRNA Expression in Alzheimer's Disease Cortex Reveals Altered miRNA Regulation. PLoS One, 2010, 5(2): e8898.
Reitz, C. et al., Epidemiology of Alzheimer Disease. Nature Rev. Neurol., 2011, 7: 137-152.

(Continued)

*Primary Examiner* — James Martinell
(74) *Attorney, Agent, or Firm* — McCarter & English, LLP; Elizabeth A. Hanley; Briana M. Erickson

(57) ABSTRACT

The invention provides a method of diagnosing Alzheimer's Disease in a subject, by determining the level of at least one miRNA in a sample derived from the subject, wherein a change in the level of the at least one miRNA relative to a suitable control is indicative of Alzheimer's Disease in the subject. Methods for monitoring the course of Alzheimer's Disease, methods of treating a subject having Alzheimer's Disease, and kits for diagnosing Alzheimer's Disease are also provided.

37 Claims, 18 Drawing Sheets

(56) References Cited

OTHER PUBLICATIONS

Shaw, L. et al., Biomarkers of neurodegeneration for diagnosis and monitoring therapeutics. Nature Rev., Drug Discovery, 2007, vol. 6: 295-303.
Tzimagiorgis, G. et al., Recovering circulating extracellular or cell-free RNA from bodily fluids. Cancer Epidemiol., 2011, 35 (6): 580-589.
Wang, W. et al., Patterns of microRNA expression in normal and early Alzheimer's disease human temporal cortex: white matter versus gray matter. Acta Neuropathol., 2011, 121(2): 193-205.
Schipper, H. et al., "MicroRNA expression in Alzheimer blood mononuclear cells." Gene Regulation and Systems Biology, 2007, vol. 1, pp. 263-274.
Office Action dated Jan. 12, 2015, issued in European Patent Application No. 2750628.5.
Office Action dated Dec. 24, 2014, issued in Chinese Patent Application No. 2012800413588.
Office Action dated May 30, 2014, issued in Australian Patent Application No. 2012275556.
Communication under Rule 71(3)EPC (Intention to Grant) dated Nov. 18, 2015, issued in European Patent Application No. 2750628.5.
Notice of Acceptance dated Jan. 22, 2016, issued in Australian Patent Application No. 2012275556.
Office Action dated May 20, 2015, issued in Australian Patent Application No. 2013204118.
Office Action dated Jan. 24, 2015, issued in Australian Patent Application No. 2012275556.
Office Action dated Sep. 14, 2015, issued in Chinese Patent Application No. 2012800413588.
Maes, O.C. et al., "MicroRNA: Implications for Alzheimer Disease and other Human CNS Disorders.", Current Genomics, 2009, 10(3)154-168.
Office Action dated Apr. 28, 2016, issued in Japanese Patent Application No. 2014-518915.
Wang, W.X. et al., "The Expression of MicroRNA miR-107 Decreases Early in Alzheimer's Disease and May Accelerate Disease Progression through Regulation of β-Site Amyloid Precursor Protein-Cleaving Enzyme 1.", J. Neurobiol., 2008, 28(5):1213-1223.
De Smaele et al., MicroRNAs as Biomarkers for CNS Cancer and Other Disorders, Brain Research, 2010, 1338:100-111.
Folstein et al., Mini-Mental State: A Practical Method for Grading the Cognitive State of Patients for the Clinician, J. Phychiat. Res., 1975, 12:189-198.
Grundman et al., Mild Cognitive Impairment Can Be Distinguished From Alzheimer Disease and Normal Aging for Clinical Trials, Arch. Neurol., 2004, 61:59-66.
Kulkarni, Meghana M., Digital Multiplexed Gene Expression Analysis Using the NanoString nCounter System, Current Protocols in Molecular Biology, Unit 25B.10 (Apr. 2011).
Kurlowicz et al., The Mini-Mental State Examination (MMSE), J. Gerontol. Nurs., 1999, 25(5):8-9.
Office Action dated Apr. 12, 2016, issued in Chinese Patent Application No. 2012800413588.
Office Action dated Oct. 19, 2016, issued in Russian Patent Application No. 2014102357.
Office Action dated Nov. 21, 2016, issued in Chinese Patent Application No. 2012800413588.
Office Action dated Nov. 30, 2016, issued in Japanese Patent Application No. 2014-518915.
Petersen et al., Mild Cognitive Impairment, Arch. Neurol., 1999, 56:303-308.
Zhou et al., The Next-Generation Sequencing Technology and Application, Protein Cell, 2010,1(6): 520-536.

\* cited by examiner

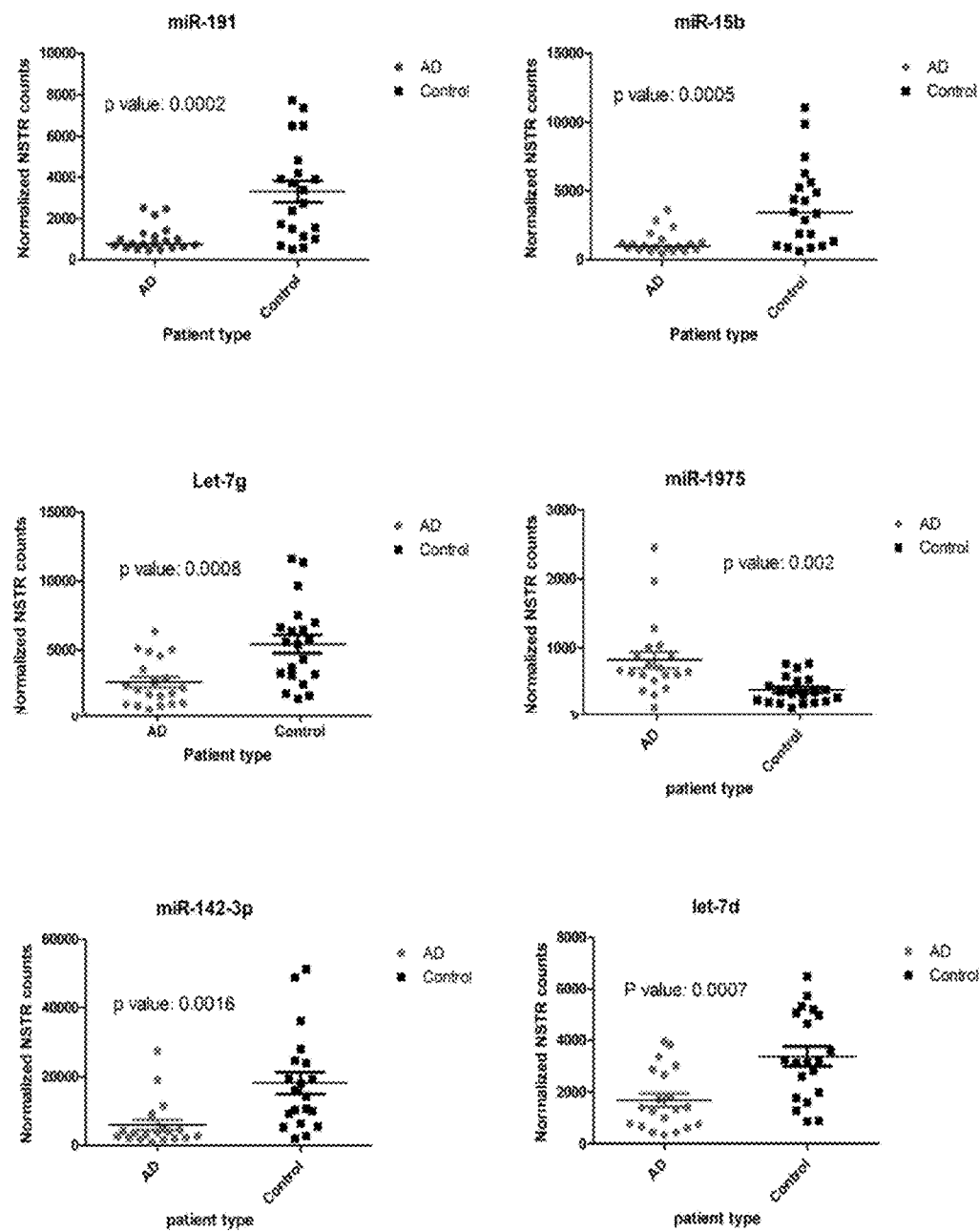
FIG. 1A: Scatter plots of individual miRNA values post normalization for 20 (AD+MCI) and 20 Control patients (Cohort 1) using Nanostring.

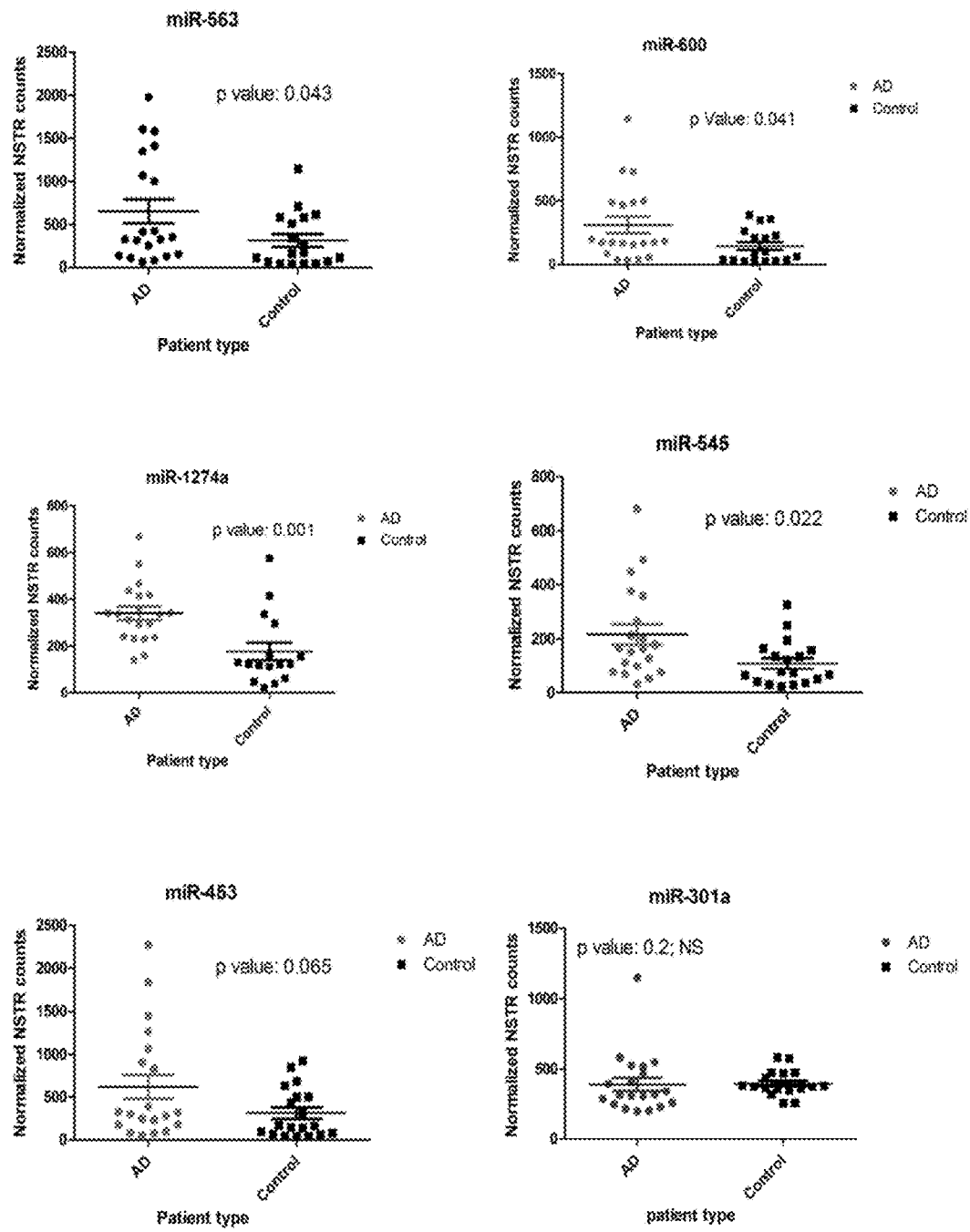
FIG. 1B: Scatter plots of individual miRNA values post normalization for 20 (AD+MCI) and 20 Control patients (Cohort 1) using Nanostring.

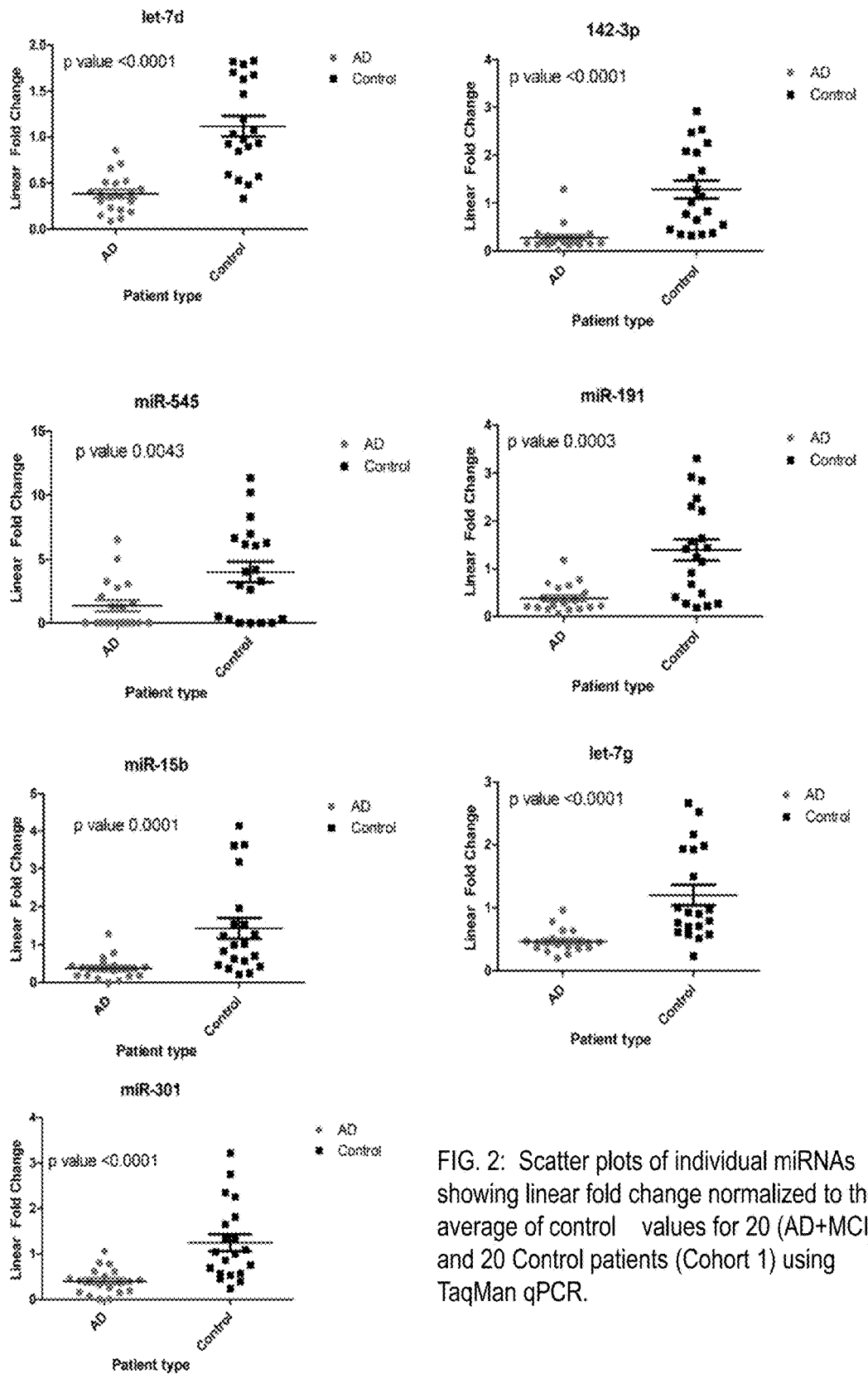
FIG. 2: Scatter plots of individual miRNAs showing linear fold change normalized to the average of control values for 20 (AD+MCI) and 20 Control patients (Cohort 1) using TaqMan qPCR.

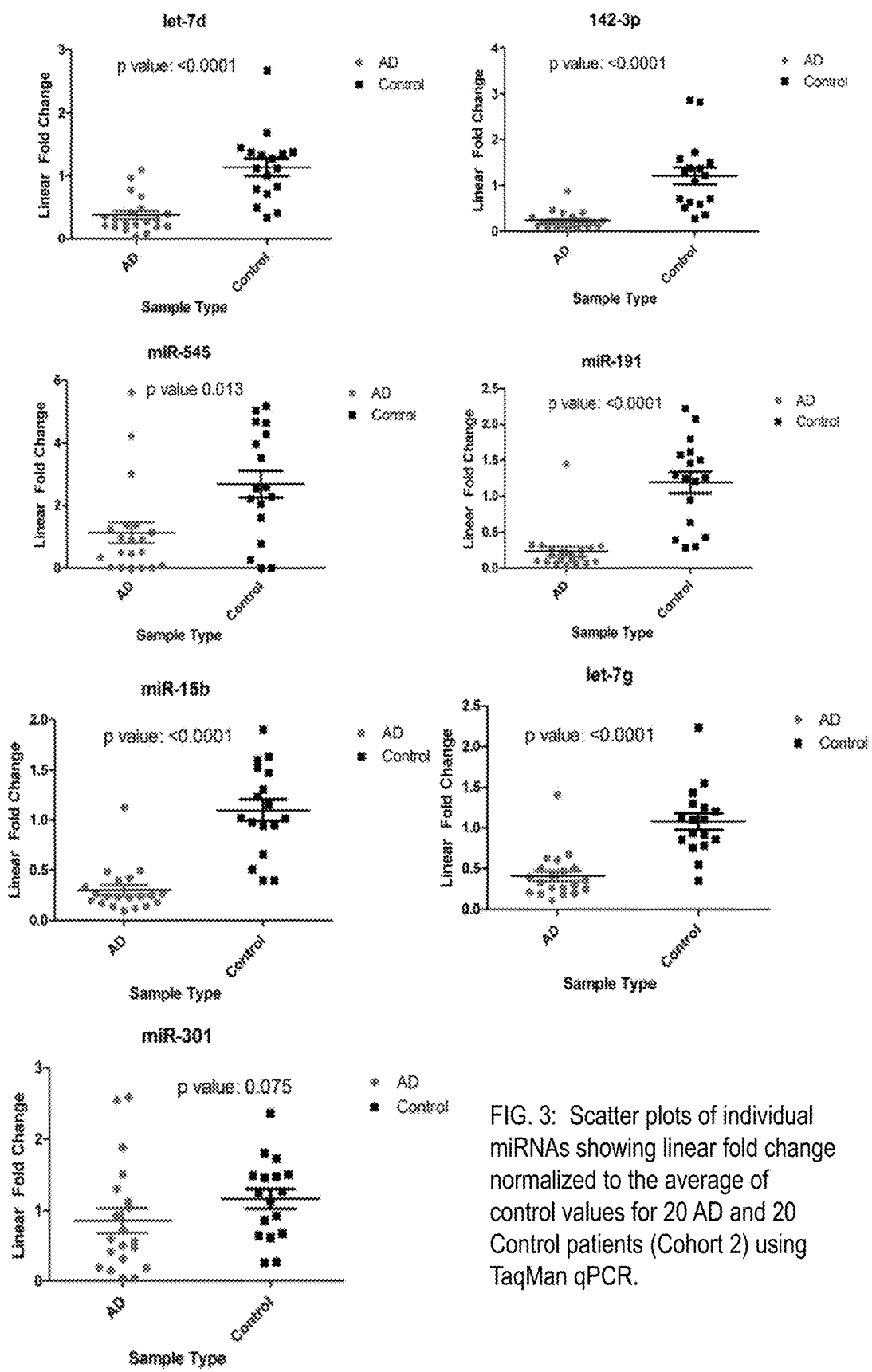
FIG. 3: Scatter plots of individual miRNAs showing linear fold change normalized to the average of control values for 20 AD and 20 Control patients (Cohort 2) using TaqMan qPCR.

FIG. 4 (Table 1): Cohort 1 Patient Samples

| Sample ID | Diagnosis | MMSE | Visit | Age | Gender |
|---|---|---|---|---|---|
| 1 | Alzheimers Disease (AD) | 17 | Visit 3 | 83 | M |
| 2 | Alzheimers Disease (AD) | 17 | Visit 3 | 80 | M |
| 3 | Alzheimers Disease (AD) | 22 | Visit 3 | 91 | M |
| 4 | Alzheimers Disease (AD) | 16 | Visit 3 | 78 | F |
| 5 | Alzheimers Disease (AD) | 23 | Visit 2 | 74 | M |
| 6 | mild cognitive impairment (MCI) | 23 | Visit 1 | 82 | F |
| 7 | mild cognitive impairment (MCI) | 23 | Visit 2 | 80 | F |
| 8 | mild cognitive impairment (MCI) | 27 | Visit 2 | 79 | F |
| 9 | Alzheimers Disease (AD) | 24 | Visit 2 | 88 | M |
| 10 | Alzheimers Disease (AD) | 18 | Visit 2 | 76 | F |
| 11 | mild cognitive impairment (MCI) | 26 | Visit 1 | 63 | F |
| 12 | Alzheimers Disease (AD) | 14 | Visit 2 | 78 | F |
| 13 | mild cognitive impairment (MCI) | 23 | Visit 2 | 79 | F |
| 14 | Alzheimers Disease (AD) | 15 | Visit 2 | 74 | M |
| 15 | mild cognitive impairment (MCI) | 25 | Visit 1 | 80 | M |
| 16 | mild cognitive impairment (MCI) | 26 | Visit 1 | 74 | F |
| 17 | mild cognitive impairment (MCI) | 26 | Visit 1 | 84 | M |
| 18 | mild cognitive impairment (MCI) | 23 | Visit 1 | 76 | M |
| 19 | Alzheimers Disease (AD) | 15 | Visit 2 | 72 | F |
| 20 | Alzheimers Disease (AD) | 16 | Visit 2 | 82 | F |
| 21 | Normal control (NC) | 30 | Visit 4 | 60 | F |
| 22 | Normal control (NC) | 30 | Visit 3 | 71 | M |
| 23 | Normal control (NC) | 27 | Visit 4 | 60 | M |
| 24 | Normal control (NC) | 30.0 | Visit 2 | 63 | F |
| 25 | Normal control (NC) | 30.0 | Visit 4 | 68 | F |
| 26 | Normal control (NC) | 30.0 | Visit 1 | 60 | M |
| 27 | Normal control (NC) | 30.0 | Visit 4 | 64 | M |
| 28 | Normal control (NC) | 27.0 | Visit 4 | 77 | M |
| 29 | Normal control (NC) | 30.0 | Visit 2 | 69 | M |
| 30 | Normal control (NC) | 30.0 | Visit 2 | 60 | F |
| 31 | Normal control (NC) | 30.0 | Visit 1 | 72 | M |
| 32 | Normal control (NC) | 30.0 | Visit 1 | 66 | F |
| 33 | Normal control (NC) | 30.0 | Visit 3 | 71 | M |
| 34 | Normal control (NC) | 29.0 | Visit 2 | 60 | F |
| 35 | Normal control (NC) | 30.0 | Visit 2 | 61 | M |
| 36 | Normal control (NC) | 30.0 | Visit 2 | 69 | M |
| 37 | Normal control (NC) | 30.0 | Visit 2 | 74 | F |
| 38 | Normal control (NC) | 30.0 | Visit 1 | 71 | F |
| 39 | Normal control (NC) | 27.0 | Visit 1 | 63 | M |
| 40 | Normal control (NC) | 30.0 | Visit 1 | 74 | F |

FIG. 5 (Table 2): miRNA Sequences and Accession Numbers

| miRNA Name | miRBASE# | Sequence | Classification |
|---|---|---|---|
| hsa-miR-142-3p | MIMAT0000434 | UGUAGUGUUUCCUACUUUAUGGA | Bio-markers |
| hsa-miR-545 | MIMAT0003165 | UCAGCAAACAUUUAUUGUGUGC | Bio-markers |
| hsa-let-7d | MIMAT0000065 | AGAGGUAGUAGGUUGCAUAGUU | Bio-markers |
| hsa-miR-191 | MIMAT0000440 | CAACGGAAUCCCAAAAGCAGCUG | Bio-markers |
| hsa-miR-301a | MIMAT0000688 | CAGUGCAAUAGUAUUGUCAAAGC | Bio-markers |
| hsa-let-7g | MIMAT0000414 | UGAGGUAGUAGUUUGUACAGUU | Bio-markers |
| hsa-miR-15b | MIMAT0000417 | UAGCAGCACAUCAUGGUUUACA | Bio-markers |
| hsa-miR-106a | MIMAT0000103 | AAAAGUGCUUACAGUGCAGGUAG | Endogenous Normalization |
| ath-159a | MIMAT0000177 | UUUGGAUUGAAGGGAGCUCUA | Spike-in Normalization/QC |

FIG. 6 (Table 3): Average fold change correlation for candidate miRNA biomarkers between Nanostring and TaqMan platforms for Cohort 1 samples (20 AD or MCI and 20 Control)

| miRNA Name | Fold Change (AD or MCI/Control) | | p-value (TaqMan validation) |
|---|---|---|---|
| | Nanostring | Singleplex TaqMan (validation) | |
| miR-191 | 0.316 | 0.27 | 0.0003 |
| miR-15b | 0.324 | 0.26 | 0.0001 |
| Let-7g | 0.487 | 0.39 | <0.0001 |
| miR-1975 | 2.1 | ND | - |
| miR-142-3p | 0.330 | 0.22 | <0.0001 |
| Let-7d | 0.498 | 0.34 | <0.0001 |
| miR-563 | 2.0 | ND | - |
| miR-600 | 2.15 | ND | - |
| miR-1274a | 2.0 | ND | - |
| miR-545 | 2.0 | 0.34 | 0.0043 |
| miR-453 | 2.0 | ND | - |
| miR-301a | 0.98 | 0.32 | <0.0001 |
| miR-126 | 0.5 | ND | - |

FIG. 7 (Table 4): Relative Ct values derived from TaqMan qPCR using Cohort 1 samples (11 AD and 20 NC)

| Sample ID | Diagnosis | let-7d | miR-142-3p | miR-545 | miR-191 | miR-15b | let-7g | miR-301a |
|---|---|---|---|---|---|---|---|---|
| 1 | Alzheimers Disease (AD) | 8.540791 | 2.01874076 | 10.40079 | 0.363541 | 6.102791 | 3.080041 | 7.398741 |
| 2 | Alzheimers Disease (AD) | 8.987076 | 3.85737609 | 11.25863 | 1.114926 | 7.078176 | 3.666526 | 8.732426 |
| 3 | Alzheimers Disease (AD) | 9.023966 | 3.13166583 | 11.11847 | 0.977966 | 6.820116 | 3.666466 | 7.797966 |
| 4 | Alzheimers Disease (AD) | 8.654064 | 3.79946354 | 11.68221 | 1.624964 | 7.634964 | 3.380114 | 8.619664 |
| 5 | Alzheimers Disease (AD) | 9.792846 | 4.80644563 | 22.07135 | 2.925596 | 8.910896 | 4.545396 | 9.141346 |
| 9 | Alzheimers Disease (AD) | 10.48618 | 5.06017738 | 20.62383 | 3.207077 | 8.149977 | 4.396227 | 8.960277 |
| 10 | Alzheimers Disease (AD) | 11.15515 | 7.64369649 | 20.1158 | 4.643996 | 11.05585 | 4.961646 | 20.1158 |
| 12 | Alzheimers Disease (AD) | 9.416403 | 4.72435258 | 12.09635 | 2.262453 | 7.971353 | 4.289153 | 8.752953 |
| 14 | Alzheimers Disease (AD) | 9.344 | 4.6593001 | 11.0176 | 2.2575 | 8.91005 | 4.0972 | 8.44655 |
| 19 | Alzheimers Disease (AD) | 11.605 | 5.29145381 | 20.56 | 3.048704 | 9.079354 | 4.128504 | 9.454554 |
| 20 | Alzheimers Disease (AD) | 10.2997 | 5.17454576 | 19.2392 | 3.316046 | 8.943146 | 4.184996 | 19.2392 |
| 21 | normal | 7.273151 | 1.32550086 | 10.12855 | -0.9376 | 4.593301 | 1.686051 | 6.252251 |
| 22 | normal | 8.078551 | 2.02195104 | 11.3447 | 0.394851 | 5.821251 | 3.063451 | 7.484751 |
| 23 | normal | 7.939583 | 1.34528261 | 10.10233 | -0.05252 | 7.694383 | 5.124883 | 8.397333 |
| 24 | normal | 7.487848 | 1.76844769 | 9.922598 | -0.1038 | 5.837348 | 2.445198 | 6.760498 |
| 25 | normal | 8.155692 | 2.19514238 | 10.71304 | 0.076742 | 6.152942 | 3.517942 | 7.052242 |
| 26 | normal | 8.142765 | 2.65471547 | 11.00932 | 0.722665 | 6.426765 | 3.360265 | 7.357215 |
| 27 | normal | 7.171389 | 1.20833879 | 9.993589 | -0.90111 | 4.602389 | 1.912039 | 6.311339 |
| 28 | normal | 7.177904 | 1.07655392 | 10.07705 | -1.117 | 4.405304 | 1.608854 | 5.801854 |
| 29 | normal | 8.202322 | 2.35257153 | 9.674122 | 0.098522 | 6.103872 | 3.173272 | 7.053222 |
| 30 | normal | 7.29832 | 0.83892007 | 9.37852 | -0.60273 | 4.78577 | 2.03822 | 7.88337 |
| 31 | normal | 7.785341 | 2.75779064 | 13.70764 | 0.297941 | 6.460341 | 3.131991 | 7.424641 |
| 32 | normal | 8.846498 | 4.02119775 | 18.1417 | 2.786098 | 7.889448 | 3.975748 | 8.281548 |
| 33 | normal | 7.998234 | 3.52878449 | 10.65888 | 1.656234 | 7.126034 | 3.020084 | 8.020384 |
| 34 | normal | 8.962006 | 3.79490644 | 14.42796 | 2.494706 | 8.515456 | 3.729506 | 8.306006 |
| 35 | normal | 8.288766 | 3.91951614 | 20.72537 | 2.491266 | 8.714366 | 3.813466 | 9.563516 |
| 36 | normal | 7.337816 | 1.63681634 | 11.15697 | -0.54093 | 5.485716 | 2.079266 | 6.623316 |
| 37 | normal | 9.629814 | 3.90871352 | 19.87646 | 3.008464 | 7.576264 | 3.809114 | 8.826014 |
| 38 | normal | 9.100729 | 3.00967889 | 14.51308 | 1.160629 | 6.719479 | 3.409629 | 7.697779 |
| 39 | normal | 7.202229 | 1.04167868 | 9.225629 | -0.69757 | 6.967829 | 2.073929 | 6.024629 |
| 40 | normal | 8.798427 | 3.25992712 | 19.86573 | 1.904427 | 7.270777 | 3.539177 | 8.613227 |

FIG. 8 (Table 5): Cohort 2 Patient Samples

| Sample ID | Diagnosis | MMSE | Visit | Age | Gender |
|---|---|---|---|---|---|
| 1 | Alzheimers Disease (AD) | 14 | 1 | 78 | F |
| 2 | Alzheimers Disease (AD) | 15 | 1 | 76 | M |
| 3 | Alzheimers Disease (AD) | 17 | 2 | 75 | M |
| 4 | Alzheimers Disease (AD) | 13 | 2 | 76 | F |
| 5 | Alzheimers Disease (AD) | 22 | 2 | 61 | M |
| 6 | Alzheimers Disease (AD) | 18 | 2 | 70 | F |
| 7 | Alzheimers Disease (AD) | 9 | 2 | 77 | F |
| 8 | Alzheimers Disease (AD) | 21 | 1 | 66 | F |
| 9 | Alzheimers Disease (AD) | 18 | 2 | 67 | F |
| 10 | Alzheimers Disease (AD) | 15 | 1 | 70 | F |
| 11 | Alzheimers Disease (AD) | 6 | 2 | 71 | F |
| 12 | Alzheimers Disease (AD) | 18 | 2 | 74 | M |
| 13 | Alzheimers Disease (AD) | 17 | 1 | 72 | M |
| 14 | Alzheimers Disease (AD) | 18 | 1 | 69 | F |
| 15 | Alzheimers Disease (AD) | 18 | 1 | 76 | M |
| 16 | Alzheimers Disease (AD) | 15 | 1 | 62 | M |
| 17 | Alzheimers Disease (AD) | 20 | 1 | 63 | M |
| 18 | Alzheimers Disease (AD) | 22 | 1 | 59 | F |
| 19 | Alzheimers Disease (AD) | 18 | 1 | 62 | M |
| 20 | Normal-Control (NC) | 30 | 2 | 62 | M |
| 21 | Normal-Control (NC) | 30 | 2 | 63 | F |
| 22 | Normal-Control (NC) | 30 | 2 | 66 | M |
| 23 | Normal-Control (NC) | 30 | 2 | 64 | F |
| 24 | Normal-Control (NC) | 29 | 2 | 62 | F |
| 25 | Normal-Control (NC) | 30 | 2 | 75 | F |
| 26 | Normal-Control (NC) | 24 | 2 | 75 | M |
| 27 | Normal-Control (NC) | 30 | 2 | 63 | F |
| 28 | Normal-Control (NC) | 30 | 2 | 60 | F |
| 29 | Normal-Control (NC) | 30 | 2 | 69 | M |
| 30 | Normal-Control (NC) | 30 | 2 | 68 | M |
| 31 | Normal-Control (NC) | 30 | 2 | 66 | M |
| 32 | Normal-Control (NC) | 30 | 1 | 64 | F |
| 33 | Normal-Control (NC) | 30 | 1 | 60 | F |
| 34 | Normal-Control (NC) | 30 | 1 | 63 | M |
| 35 | Normal-Control (NC) | 29 | 1 | 67 | M |
| 36 | Normal-Control (NC) | 30 | 1 | 68 | M |
| 37 | Alzheimers Disease (AD) | 16 | 2 | 62 | M |

FIG. 9 (Table 6): Average fold change (normalized to average Control values) correlation for candidate miRNA biomarkers between Cohort 1 and Cohort 2 using TaqMan qPCR

| miRNA Name | Fold Change (AD/Control) | | |
|---|---|---|---|
| | Singleplex TaqMan (Cohort1) | Singleplex TaqMan (Cohort2) | p-value (Cohort2) |
| miR-191 | 0.27 | 0.2 | <0.0001 |
| miR-15b | 0.26 | 0.27 | <0.0001 |
| miR-142-3p | 0.22 | 0.2 | <0.0001 |
| Let-7g | 0.39 | 0.38 | <0.0001 |
| Let-7d | 0.34 | 0.3 | <0.0001 |
| miR-301a | 0.32 | 0.7 | 0.075 |
| miR-545 | 0.34 | 0.42 | 0.013 |

FIG. 10 (Table 7): Relative Ct values derived from TaqMan qPCR using Cohort 2 samples (20 AD and 17 NC)

|  | Sample ID | let-7d | miR-191 | miR-301a | miR-545 | let-7g | miR-15b | miR-142-3p |
|---|---|---|---|---|---|---|---|---|
| AD | 1 | 9.824295 | 3.098545 | 6.976695 | 18.7577 | 5.202645 | 8.820145 | 4.099645 |
| AD | 2 | 12.89131 | 4.622906 | 8.268856 | 21.82076 | 6.257256 | 9.206956 | 5.283656 |
| AD | 3 | 10.52676 | 5.147009 | 8.432209 | 16.36401 | 5.782509 | 9.066209 | 5.114409 |
| AD | 4 | 10.92046 | 4.689505 | 9.087305 | 13.52616 | 5.633905 | 9.793255 | 4.450655 |
| AD | 5 | 11.6412 | 3.934905 | 9.312455 | 13.4799 | 5.857755 | 9.294355 | 4.289305 |
| AD | 6 | 10.35952 | 3.218769 | 7.737069 | 12.19887 | 5.350119 | 8.726569 | 3.922869 |
| AD | 7 | 10.42707 | 2.989324 | 7.409774 | 12.60472 | 4.944774 | 7.737674 | 2.931624 |
| AD | 8 | 9.120479 | 2.975929 | 6.952529 | 12.54638 | 4.571929 | 8.295279 | 3.727279 |
| AD | 9 | 10.16382 | 5.406315 | 10.69702 | 22.67052 | 6.290865 | 10.12647 | 5.468315 |
| AD | 10 | 9.805652 | 3.448502 | 9.156852 | 14.09495 | 5.438552 | 8.792552 | 3.973952 |
| AD | 11 | 8.117455 | 3.774155 | 9.403655 | 10.90145 | 4.812105 | 8.654655 | 3.231055 |
| AD | 12 | 8.645876 | 2.920626 | 7.949176 | 12.03438 | 4.845676 | 7.780126 | 2.740676 |
| AD | 13 | 9.641232 | 3.356682 | 8.810432 | 17.63633 | 4.512332 | 8.080632 | 3.316432 |
| AD | 14 | 9.340862 | 4.311362 | 9.979162 | 12.04816 | 5.784462 | 8.785662 | 4.125662 |
| AD | 15 | 8.436459 | 3.708709 | 8.162859 | 12.67881 | 4.411259 | 7.979409 | 2.895409 |
| AD | 16 | 9.406506 | 5.208356 | 10.67176 | 10.42276 | 5.118006 | 9.577656 | 4.690756 |
| AD | 17 | 9.9741 | 4.8933 | 12.92685 | 21.51865 | 7.0431 | 8.6345 | 4.6715 |
| AD | 18 | 10.24597 | 4.318268 | 11.00422 | 13.65662 | 6.088668 | 8.856068 | 4.787318 |
| AD | 19 | 7.943852 | 0.738802 | 9.593602 | 10.009 | 3.351652 | 6.555602 | 1.829852 |
| Control | 20 | 7.615908 | 0.954308 | 7.540308 | 10.27971 | 4.076908 | 6.346108 | 1.246608 |
| Control | 21 | 7.538733 | 0.724883 | 8.446883 | 10.26723 | 3.465433 | 6.172333 | 1.047233 |
| Control | 22 | 7.724992 | 0.936692 | 8.541842 | 11.45884 | 3.970342 | 6.816892 | 2.280492 |
| Control | 23 | 7.317299 | 0.682199 | 7.735899 | 10.51125 | 3.703249 | 6.764599 | 2.131749 |
| Control | 24 | 7.630084 | 0.428384 | 7.473584 | 10.67928 | 3.936634 | 6.050384 | 0.981734 |
| Control | 25 | 9.104217 | 1.340517 | 8.891017 | 14.40147 | 4.064617 | 6.708767 | 2.137517 |
| Control | 26 | 7.908233 | 0.121183 | 8.003333 | 11.14918 | 3.514683 | 6.703883 | 0.851033 |
| Control | 27 | 7.910895 | 0.215295 | 8.152195 | 11.30549 | 3.211795 | 6.021045 | 1.358545 |
| Control | 28 | 7.612373 | 0.996223 | 7.756173 | 11.12332 | 3.675973 | 6.520023 | 1.516723 |
| Control | 29 | 9.364145 | 3.015545 | 10.2347 | 11.8139 | 5.328945 | 8.050045 | 3.499895 |
| Control | 30 | 9.666285 | 3.083535 | 9.025385 | 20.51988 | 4.704485 | 8.046835 | 3.117535 |
| Control | 31 | 8.413839 | 2.617189 | 8.961839 | 12.85379 | 4.197289 | 7.335889 | 2.402489 |
| Control | 32 | 8.558735 | 2.492235 | 10.18563 | 24.08808 | 4.250335 | 7.707735 | 2.604835 |
| Control | 33 | 8.339448 | 0.579248 | 7.986598 | 10.1653 | 3.573948 | 6.122248 | 0.138598 |
| Control | 34 | 7.666189 | 0.903339 | 7.761739 | 10.40154 | 3.324539 | 6.429139 | 1.181639 |
| Control | 35 | 6.645039 | 0.617089 | 7.084739 | 10.12354 | 2.686589 | 5.804439 | 0.117289 |
| Control | 36 | 8.074962 | 1.928062 | 7.781412 | 11.35086 | 3.708162 | 6.809062 | 1.180012 |
| AD | 37 | 10.51991 | 6.314958 | 12.85451 | 12.31906 | 6.176558 | 9.642558 | 4.850308 |

FIG. 11A (Table 8A): Candidate miRNA Biomarker Signatures

| miRNA signatures |
|---|
| miR-545 let-7g miR-15b |
| miR-545 miR-15b |
| miR-301a miR-545 let-7g miR-15b |
| miR-191 miR-15b |
| let-7g miR-15b |
| miR-191 miR-301aa miR-545 |
| miR-301aa let-7g miR-15b |
| miR-191 miR-301a miR-545 miR-15b |
| miR-191 |
| miR-15b |
| miR-191 miR-301a |
| miR-191 miR-545 |
| miR-191 let-7g |
| miR-301a let-7g |
| miR-191 miR-301a let-7g |
| miR-191 miR-545 miR-15b |
| miR-191 let-7g miR-15b |
| miR-191 miR-301a miR-545 let-7g |
| miR-191 miR-301a let-7g miR-15b |
| miR-191 miR-545 let-7g miR-15b |
| miR-191 miR-301a miR-545 let-7g miR-15b |
| let-7d miR-545 |
| let-7d miR-301a miR-545 |
| let-7d miR-545 miR-15b |
| miR-191 miR-301a miR-15b |
| miR-191 miR-545 let-7g |
| miR-301a miR-545 miR-15b |
| let-7d miR-301a miR-545 miR-15b |
| let-7d |
| miR-142-3p |
| let-7d miR-301a |
| let-7d miR-142-3p |
| miR-301a miR-15b |
| miR-301a miR-142-3p |
| let-7g miR-142-3p |
| let-7d miR-191 miR-545 |
| let-7d miR-301a miR-142-3p |
| let-7d miR-545 miR-142-3p |
| let-7d let-7g miR-142-3p |
| miR-301a miR-545 let-7g |
| miR-301a let-7g miR-142-3p |
| miR-545 let-7g miR-142-3p |
| let-7d miR-301a miR-545 miR-142-3p |
| let-7d miR-301a let-7g miR-142-3p |
| let-7d miR-545 let-7g miR-15b |
| let-7d miR-545 miR-15b miR-142-3p |
| let-7d let-7g miR-15b miR-142-3p |
| miR-301a miR-545 let-7g miR-142-3p |
| miR-545 let-7g miR-15b miR-142-3p |

FIG. 11B (Table 8B): Candidate miRNA Biomarker Signatures

| Signature |
|---|
| let-7d miR-301a miR-545 let-7g miR-15b |
| let-7d miR-301a miR-545 miR-15b miR-142-3p |
| let-7d miR-301a let-7g miR-15b miR-142-3p |
| miR-301a miR-545 let-7g miR-15b miR-142-3p |
| let-7d let-7g |
| let-7d miR-15b |
| miR-545 miR-142-3p |
| let-7d miR-301a let-7g |
| let-7d miR-301a miR-15b |
| let-7d miR-545 let-7g |
| let-7d let-7g miR-15b |
| let-7d miR-15b miR-142-3p |
| miR-301a miR-545 miR-142-3p |
| let-7g miR-15b miR-142-3p |
| let-7d miR-191 miR-301a miR-545 |
| let-7d miR-191 miR-545 let-7g |
| let-7d miR-191 miR-545 miR-15b |
| let-7d miR-301a miR-545 let-7g |
| let-7d miR-301a miR-15b miR-142-3p |
| miR-301a let-7g miR-15b miR-142-3p |
| let-7d miR-191 miR-301a miR-545 let-7g |
| let-7d miR-191 miR-301a miR-545 miR-15b |
| let-7d miR-191 miR-545 let-7g miR-15b |
| let-7d miR-191 miR-301a miR-545 let-7g miR-15b |
| let-7g |
| miR-545 let-7g |
| miR-545 miR-15b miR-142-3p |
| let-7d miR-301a let-7g miR-15b |
| let-7d miR-545 let-7g miR-142-3p |
| miR-301a miR-545 miR-15b miR-142-3p |
| let-7d miR-301a miR-545 let-7g miR-142-3p |
| let-7d miR-545 let-7g miR-15b miR-142-3p |
| let-7d miR-301a miR-545 let-7g miR-15b miR-142-3p |
| let-7d miR-191 let-7g |
| let-7d miR-191 |
| miR-15b miR-142-3p |
| miR-301a miR-15b miR-142-3p |
| let-7d miR-191 miR-15b |
| let-7d miR-191 miR-301a let-7g |
| let-7d miR-191 miR-301a |
| let-7d miR-191 miR-301a miR-15b |
| let-7d miR-191 miR-545 miR-142-3p |
| let-7d miR-191 let-7g miR-15b |
| let-7d miR-191 miR-301a miR-545 miR-142-3p |
| let-7d miR-191 miR-301a let-7g miR-15b |
| let-7d miR-191 miR-545 let-7g miR-142-3p |
| let-7d miR-191 miR-545 miR-15b miR-142-3p |
| let-7d miR-191 miR-301a miR-545 let-7g miR-142-3p |
| let-7d miR-191 miR-301a miR-545 miR-15b miR-142-3p |
| let-7d miR-191 miR-545 let-7g miR-15b miR-142-3p |

FIG. 11C (Table 8C): Candidate miRNA Biomarker Signatures

| |
|---|
| let-7d miR-191 miR-301a miR-545 let-7g miR-15b miR-142-3p |
| miR-301a |
| miR-301a miR-545 |
| miR-545 |
| let-7d miR-191 miR-142-3p |
| let-7d miR-191 miR-301a miR-142-3p |
| let-7d miR-191 let-7g miR-142-3p |
| let-7d miR-191 miR-15b miR-142-3p |
| let-7d miR-191 miR-301a let-7g miR-142-3p |
| let-7d miR-191 miR-301a miR-15b miR-142-3p |
| let-7d miR-191 let-7g miR-15b miR-142-3p |
| miR-191 miR-545 let-7g miR-15b miR-142-3p |
| let-7d miR-191 miR-301a let-7g miR-15b miR-142-3p |
| miR-191 miR-301a miR-545 let-7g miR-15b miR-142-3p |
| miR-191 let-7g miR-15b miR-142-3p |
| miR-191 miR-301a let-7g miR-15b miR-142-3p |
| miR-191 miR-142-3p |
| miR-191 miR-301a miR-142-3p |
| miR-191 miR-545 miR-142-3p |
| miR-191 let-7g miR-142-3p |
| miR-191 miR-15b miR-142-3p |
| miR-191 miR-301a miR-545 miR-142-3p |
| miR-191 miR-301a let-7g miR-142-3p |
| miR-191 miR-301a miR-15b miR-142-3p |
| miR-191 miR-545 let-7g miR-142-3p |
| miR-191 miR-545 miR-15b miR-142-3p |
| miR-191 miR-301a miR-545 let-7g miR-142-3p |
| miR-191 miR-301a miR-545 miR-15b miR-142-3p |

FIG. 12A (Table 9A): Accuracy, Specificity, Sensitivity and AUC (Area Under the Curve) for miRNA signatures having an accuracy of >75%, using Cohort 2 samples for prediction

| miRNA signature | Accuracy (%) | Sensitivity (%) | Specificity (%) | AUC |
|---|---|---|---|---|
| miR-545 let-7g miR-15b | 94.5946 | 95 | 94.11765 | 0.952941 |
| miR-545 miR-15b | 91.8919 | 90 | 94.11765 | 0.964706 |
| miR-301a miR-545 let-7g miR-15b | 91.8919 | 95 | 88.2353 | 0.964706 |
| miR-191 miR-15b | 89.18919 | 95 | 82.35294 | 0.961765 |
| let-7g miR-15b | 89.18919 | 95 | 82.35294 | 0.941177 |
| miR-191 miR-301a miR-545 | 89.18919 | 95 | 82.35294 | 0.955882 |
| miR-301a let-7g miR-15b | 89.18919 | 95 | 82.35294 | 0.932353 |
| miR-191 miR-301a miR-545 miR-15b | 89.18919 | 95 | 82.35294 | 0.955882 |
| miR-191 | 86.48649 | 95 | 76.47059 | 0.952941 |
| miR-15b | 86.48649 | 85 | 88.2353 | 0.955882 |
| miR-191 miR-301a | 86.48649 | 95 | 76.47059 | 0.929412 |
| miR-191 miR-545 | 86.48649 | 95 | 76.47059 | 0.952941 |
| miR-191 let-7g | 86.48649 | 95 | 76.47059 | 0.938235 |
| miR-301a let-7g | 86.48649 | 95 | 76.47059 | 0.920588 |
| miR-191 miR-301a let-7g | 86.48649 | 95 | 76.47059 | 0.932353 |
| miR-191 miR-545 miR-15b | 86.48649 | 95 | 76.47059 | 0.952941 |
| miR-191 let-7g miR-15b | 86.48649 | 95 | 76.47059 | 0.95 |
| miR-191 miR-301a miR-545 let-7g | 86.48649 | 95 | 76.47059 | 0.95 |
| miR-191 miR-301a let-7g miR-15b | 86.48649 | 95 | 76.47059 | 0.935294 |
| miR-191 miR-545 let-7g miR-15b | 86.48649 | 95 | 76.47059 | 0.952941 |
| miR-191 miR-301a miR-545 let-7g miR-15b | 86.48649 | 95 | 76.47059 | 0.95 |
| let-7d miR-545 | 83.78378 | 80 | 88.2353 | 0.932353 |
| let-7d miR-301a miR-545 | 83.78378 | 80 | 88.2353 | 0.935294 |
| let-7d miR-545 miR-15b | 83.78378 | 80 | 88.2353 | 0.938235 |
| miR-191 miR-301a miR-15b | 83.78378 | 85 | 82.35294 | 0.944118 |
| miR-191 miR-545 let-7g | 83.78378 | 95 | 70.58824 | 0.952941 |
| miR-301a miR-545 miR-15b | 83.78378 | 75 | 94.11765 | 0.967647 |
| let-7d miR-301a miR-545 miR-15b | 83.78378 | 80 | 88.2353 | 0.935294 |
| let-7d | 81.08108 | 75 | 88.2353 | 0.923529 |
| miR-142-3p | 81.08108 | 65 | 100 | 0.955882 |
| let-7d miR-301a | 81.08108 | 75 | 88.2353 | 0.923529 |
| let-7d miR-142-3p | 81.08108 | 75 | 88.2353 | 0.929412 |
| miR-301a miR-15b | 81.08108 | 70 | 94.11765 | 0.941177 |
| miR-301a miR-142-3p | 81.08108 | 65 | 100 | 0.955882 |
| let-7g miR-142-3p | 81.08108 | 65 | 100 | 0.955882 |
| let-7d miR-191 miR-545 | 81.08108 | 75 | 88.2353 | 0.929412 |
| let-7d miR-301a miR-142-3p | 81.08108 | 75 | 88.2353 | 0.932353 |
| let-7d miR-545 miR-142-3p | 81.08108 | 70 | 94.11765 | 0.958824 |
| let-7d let-7g miR-142-3p | 81.08108 | 70 | 94.11765 | 0.926471 |
| miR-301a miR-545 let-7g | 81.08108 | 95 | 64.70588 | 0.926471 |
| miR-301a let-7g miR-142-3p | 81.08108 | 65 | 100 | 0.955882 |
| miR-545 let-7g miR-142-3p | 81.08108 | 70 | 94.11765 | 0.967647 |

FIG. 12B (Table 9B): Accuracy, Specificity, Sensitivity and AUC (Area Under the Curve) for miRNA signatures having an accuracy of >75%, using Cohort 2 samples for prediction

| miRNA signature | Accuracy (%) | Sensitivity (%) | Specificity (%) | AUC |
|---|---|---|---|---|
| let-7d miR-301a miR-545 miR-142-3p | 81.08108 | 70 | 94.11765 | 0.958824 |
| let-7d miR-301a let-7g miR-142-3p | 81.08108 | 70 | 94.11765 | 0.932353 |
| let-7d miR-545 let-7g miR-15b | 81.08108 | 70 | 94.11765 | 0.923529 |
| let-7d miR-545 miR-15b miR-142-3p | 81.08108 | 70 | 94.11765 | 0.958824 |
| let-7d let-7g miR-15b miR-142-3p | 81.08108 | 75 | 88.2353 | 0.935294 |
| miR-301a miR-545 let-7g miR-142-3p | 81.08108 | 70 | 94.11765 | 0.967647 |
| miR-545 let-7g miR-15b miR-142-3p | 81.08108 | 70 | 94.11765 | 0.964706 |
| let-7d miR-301a miR-545 let-7g miR-15b | 81.08108 | 70 | 94.11765 | 0.923529 |
| let-7d miR-301a miR-545 miR-15b miR-142-3p | 81.08108 | 70 | 94.11765 | 0.958824 |
| let-7d miR-301a let-7g miR-15b miR-142-3p | 81.08108 | 75 | 88.2353 | 0.935294 |
| miR-301a miR-545 let-7g miR-15b miR-142-3p | 81.08108 | 70 | 94.11765 | 0.961765 |
| let-7d let-7g | 78.37838 | 70 | 88.2353 | 0.911765 |
| let-7d miR-15b | 78.37838 | 75 | 82.35294 | 0.902941 |
| miR-545 miR-142-3p | 78.37838 | 65 | 94.11765 | 0.967647 |
| let-7d miR-301a let-7g | 78.37838 | 70 | 88.2353 | 0.908824 |
| let-7d miR-301a miR-15b | 78.37838 | 75 | 82.35294 | 0.905882 |
| let-7d miR-545 let-7g | 78.37838 | 70 | 88.2353 | 0.926471 |
| let-7d let-7g miR-15b | 78.37838 | 70 | 88.2353 | 0.9 |
| let-7d miR-15b miR-142-3p | 78.37838 | 70 | 88.2353 | 0.935294 |
| miR-301a miR-545 miR-142-3p | 78.37838 | 65 | 94.11765 | 0.967647 |
| let-7g miR-15b miR-142-3p | 78.37838 | 65 | 94.11765 | 0.952941 |
| let-7d miR-191 miR-301a miR-545 | 78.37838 | 70 | 88.2353 | 0.920588 |
| let-7d miR-191 miR-545 let-7g | 78.37838 | 70 | 88.2353 | 0.926471 |
| let-7d miR-191 miR-545 miR-15b | 78.37838 | 70 | 88.2353 | 0.920588 |
| let-7d miR-301a miR-545 let-7g | 78.37838 | 70 | 88.2353 | 0.926471 |
| let-7d miR-301a miR-15b miR-142-3p | 78.37838 | 70 | 88.2353 | 0.935294 |
| miR-301a let-7g miR-15b miR-142-3p | 78.37838 | 65 | 94.11765 | 0.952941 |
| let-7d miR-191 miR-301a miR-545 let-7g | 78.37838 | 70 | 88.2353 | 0.920588 |
| let-7d miR-191 miR-301a miR-545 miR-15b | 78.37838 | 70 | 88.2353 | 0.920588 |
| let-7d miR-191 miR-545 let-7g miR-15b | 78.37838 | 65 | 94.11765 | 0.914706 |
| let-7d miR-191 miR-301a miR-545 let-7g miR-15b | 78.37838 | 65 | 94.11765 | 0.905882 |
| let-7g | 75.67568 | 95 | 52.94118 | 0.926471 |
| miR-545 let-7g | 75.67568 | 95 | 52.94118 | 0.926471 |
| miR-545 miR-15b miR-142-3p | 75.67568 | 60 | 94.11765 | 0.967647 |
| let-7d miR-301a let-7g miR-15b | 75.67568 | 70 | 82.35294 | 0.9 |
| let-7d miR-545 let-7g miR-142-3p | 75.67568 | 60 | 94.11765 | 0.952941 |
| miR-301a miR-545 miR-15b miR-142-3p | 75.67568 | 60 | 94.11765 | 0.967647 |
| let-7d miR-301a miR-545 let-7g miR-142-3p | 75.67568 | 60 | 94.11765 | 0.952941 |
| let-7d miR-545 let-7g miR-15b miR-142-3p | 75.67568 | 60 | 94.11765 | 0.955882 |
| let-7d miR-301a miR-545 let-7g miR-15b miR-142-3p | 75.67568 | 60 | 94.11765 | 0.955882 |

FIG. 13 (Table 10): Accuracy, Specificity, Sensitivity and AUC (Area under the Curve) for the top 8 miRNA signature combinations using Cohort 2 samples for prediction

| miRNA signature | Accuracy | Specificity | Sensitivity | AUC (Area under the curve) |
|---|---|---|---|---|
| miR-545, let7g and miR-15b | 94.6% | 94.1% | 95% | 0.953 |
| miR-15b and miR-545 | 91.9% | 94.1% | 90% | 0.96 |
| miR-301a, miR-545, let-7g and miR-15b | 91.9% | 88.2% | 95% | 0.96 |
| miR-191 and miR-15b | 89.2% | 82.3% | 95% | 0.96 |
| Let-7g and miR-15b | 89.2% | 82.3% | 95% | 0.94 |
| miR-191, miR-301a and miR-545 | 89.2% | 82.3% | 95% | 0.96 |
| miR-301a, let-7g and miR-15b | 89.2% | 82.3% | 95% | 0.93 |
| miR-191, miR-301a, miR-545 and miR-15b | 89.2% | 82.3% | 95% | 0.96 |

FIG. 14 (Table 11): Accuracy, Specificity, Sensitivity and AUC (Area under the Curve, maximum possible value of 1) for each candidate miRNA individually using Cohort 2 samples (20 AD and 17 Control) for prediction

| Individual miRNA signature | Accuracy | Sensitivity | Specificity | AUC (Area under the curve) |
|---|---|---|---|---|
| miR-191 | 86.5% | 95% | 76% | 0.95 |
| miR-15b | 86.5% | 85% | 88% | 0.95 |
| miR-142-3p | 81.1% | 65% | 100% | 0.95 |
| Let-7g | 75.7% | 95% | 53% | 0.92 |
| Let-7d | 81.1% | 75% | 88% | 0.92 |
| miR-301a | 59.5% | 25% | 100% | 0.67 |
| miR-545 | 51.4% | 20% | 88% | 0.74 |

SEQUENCE LISTING

```
<160> NUMBER OF SEQ ID NOS: 10

<210> SEQ ID NO 1
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
uuguggcgag cggaauggaa u                                              21

<210> SEQ ID NO 2
<211> LENGTH: 23
<212> TYPE: RNA
<213> ORGANISM: Homo sapiens

<400> SEQUENCE: 2
uguaguguuu ccuacuuuau gga                                            23

<210> SEQ ID NO 3
<211> LENGTH: 22
<212> TYPE: RNA
<213> ORGANISM: Homo sapiens

<400> SEQUENCE: 3
ucagcaaaca uuuauugugu gc                                             22

<210> SEQ ID NO 4
<211> LENGTH: 22
<212> TYPE: RNA
<213> ORGANISM: Homo sapiens
```

-continued

```
<400> SEQUENCE: 4
agagguagua gguugcauag uu                                              22

<210> SEQ ID NO 5
<211> LENGTH: 23
<212> TYPE: RNA
<213> ORGANISM: Homo sapiens

<400> SEQUENCE: 5
caacggaauc ccaaaagcag cug                                             23

<210> SEQ ID NO 6
<211> LENGTH: 23
<212> TYPE: RNA
<213> ORGANISM: Homo sapiens

<400> SEQUENCE: 6
cagugcaaua guauugucaa agc                                             23

<210> SEQ ID NO 7
<211> LENGTH: 22
<212> TYPE: RNA
<213> ORGANISM: Homo sapiens

<400> SEQUENCE: 7
ugagguagua guuuguacag uu                                              22

<210> SEQ ID NO 8
<211> LENGTH: 22
<212> TYPE: RNA
<213> ORGANISM: Homo sapiens

<400> SEQUENCE: 8
uagcagcaca ucaugguuua ca                                              22

<210> SEQ ID NO 9
<211> LENGTH: 23
<212> TYPE: RNA
<213> ORGANISM: Homo sapiens

<400> SEQUENCE: 9
aaaagugcuu acagugcagg uag                                             23

<210> SEQ ID NO 10
<211> LENGTH: 21
<212> TYPE: RNA
<213> ORGANISM: Arabidopsis thaliana

<400> SEQUENCE: 10
uuuggauuga agggagcucu a                                               21
```

MICRORNA BIOMARKERS INDICATIVE OF ALZHEIMER'S DISEASE

RELATED APPLICATIONS

This application is a 35 U.S.C. 371 national stage filing of International Application No. PCT/US2012/044202 filed Jun. 26, 2012, which claims priority to U.S. Provisional Application No. 61/501,720 filed on Jun. 27, 2011. The entire contents of the aforementioned applications are hereby incorporated by reference.

BACKGROUND

Alzheimer's Disease is a progressive disease of the human central nervous system. It is manifested by dementia, typically in the elderly, and symptoms include disorientation, loss of memory, difficulty with language, calculation, or visual-spatial skills, and by psychiatric manifestations. Alzheimer's Disease is associated with degenerating neurons in several regions of the brain. The neuropathology of Alzheimer's Disease is characterized by the presence of amyloid plaques, neurofibrillary tangles, synaptic loss and selective neuronal cell death. Amyloid plaques result from abnormal levels of extracellular amyloid beta peptide, while neurofibrillary tangles are associated with the presence of intracellular hyperphosphorylated tau protein. Symptoms typically first manifest clinically with a decline in memory followed by deterioration in other cognitive functions, and by abnormal behavior. Approximately 24 million people worldwide have dementia, of which the majority (~60%) is due to Alzheimer's Disease (Ferri C. P. et al. (2005) Lancet 366(9503):2112-2117). More than 5 million Americans are estimated to have Alzheimer's Disease, and it is projected that this number will increase to 14.3 million by mid-century, representing a 350 percent increase from 2000. The increasing number of dementia patients in the developed world will place an enormous burden on society and the health care system.

Early diagnosis is an essential step in the treatment of Alzheimer's Disease, as early diagnosis allows subjects to receive drugs that may slow disease progression. Alzheimer's Disease is currently diagnosed using a combination of clinical criteria, which may include a neurological exam, mental status tests, and brain imaging. A diagnosis of Alzheimer's Disease is often made by eliminating other dementias. Based on these criteria, an accurate diagnosis can be difficult, especially for patients having mild or early-stage Alzheimer's Disease. An unambiguous diagnosis may be made by examining the pathology of brain tissue, but this is only feasible posthumously. Accordingly, a need exists for markers that are indicative of Alzheimer's Disease which may be used in diagnostic applications.

SUMMARY

The present invention provides novel miRNA biomarkers which are indicative of Alzheimer's Disease, and which may be used to accurately diagnose Alzheimer's Disease in a subject. These biomarkers include miR-191, miR-15b, miR-142-3p, Let-7g, Let-7d, miR-301a and miR-545. In some embodiments, the methods entail detection of extracellular, circulating miRNAs in a suitable sample, preferably blood, plasma, serum, urine, or saliva.

Accordingly, in a first aspect, the invention provides a method of diagnosing Alzheimer's Disease in a subject by determining the level of at least one miRNA in a sample containing circulating miRNA derived from the subject, wherein the at least one miRNA is miR-191, miR-15b, miR-142-3p, Let-7g, Let-7d, or combinations thereof, and wherein a difference in the level of the at least one miRNA versus that in a normal subject as determined relative to a suitable control is indicative of Alzheimer's Disease in the subject. For example, in one embodiment, the method includes determining the level of at least one miRNA in a sample containing circulating miRNA derived from the subject, wherein the at least one miRNA is miR-191, miR-15b, miR-142-3p, Let-7g, Let-7d, or combinations thereof, and wherein a decrease in the level of the at least one miRNA relative to a control is indicative of Alzheimer's Disease in the subject. Optionally, the method may further comprise providing a diagnosis that the subject has or does not have Alzheimer's Disease based on the level of at least one miRNA in the sample. In one embodiment, the method may further comprise correlating a difference in the level or levels of at least one miRNA relative to a suitable control with a diagnosis of Alzheimer's Disease in the subject.

In one embodiment, the method comprises determining the level of one miRNA, e.g., miR-191, miR-15b, miR-142-3p, Let-7g or Let-7d, in the sample, wherein the difference in the level of the miRNA versus that in a normal subject is a decrease.

In another embodiment, the method comprises determining the level of two or more miRNAs in the sample. In this embodiment, the method may further comprise determining the level of miR-301a, miR-545, or miR-301a and miR-545 in the sample. For example, at least one miRNA can be selected from miR-191, miR-15b, miR-142-3p, Let-7g, Let-7d, or combinations thereof, and optionally, at least one mRNA can be selected from miR-301a, miR-545, or miR-301a and miR-545. In one embodiment, the method involves determining the level of one of the following combinations of miRNAs: miR-545, let7g, and miR-15b; miR-15b and miR-545; miR-301a, miR-545, let-7g and miR-15b; miR-191 and miR-15b; Let-7g and miR-15b; miR-191, miR-301a, and miR-545; miR-301a, let-7g, and miR-15b; and miR-191, miR-301a, miR-545, and miR-15b.

In one particular embodiment, the method may comprise determining the levels of two or more miRNAs in a sample containing circulating miRNA from the subject, comparing the levels of the two or more miRNAs in the sample to a set of data representing levels of the same miRNAs present in normal subjects and subjects having Alzheimer's Disease, and diagnosing the subject as having or not having Alzheimer's Disease based on the comparison. In some embodiments, the two or more miRNAs may include the following combinations: miR-545, let7g, and miR-15b; miR-15b and miR-545; miR-301a, miR-545, let-7g and miR-15b; miR-191 and miR-15b; Let-7g and miR-15b; miR-191, miR-301a, and miR-545; miR-301a, let-7g, and miR-15b; and miR-191, miR-301a, miR-545, and miR-15b.

The method may optionally include performing at least one additional test to facilitate the diagnosis of Alzheimer's Disease. In certain embodiments, the additional test may be one or more of the mini-mental state examination (MMSE), the mini-cog test, the ADAS-cog test, and the clock-drawing test. Optionally or in addition, additional testing may include detecting or assessing at least one additional biomarker for Alzheimer's Disease.

The method may optionally include administering a therapeutically effective amount of at least one Alzheimer's therapeutic to the subject. In certain embodiments, the Alzheimer's therapeutic may be Razadyne® (galantamine), Exelon® (rivastigmine), or Aricept® (donepezil). In a particular embodiment, the Alzheimer's therapeutic is donepezil or a pharmaceutically acceptable salt or ester thereof (e.g., donepezil hydrochloride).

The level of a miRNA may be detected by any suitable method. For example, a miRNA may be detected using an agent which specifically hybridizes to the miRNA. In certain embodiments, the level of a miRNA may be detected using amplification methods, hybridization methods, and/or sequencing methods. In one embodiment, the level of miRNA is detected using quantitative PCR.

In another aspect, the invention provides a method of diagnosing Alzheimer's Disease in a subject, comprising measuring the level of at least one miRNA in a blood-derived sample from the subject, wherein the at least one miRNA is miR-191, miR-15b, miR-142-3p, Let-7g, Let-7d, or combinations thereof, and correlating a difference in the level or levels in the subject relative to a suitable control with a diagnosis of Alzheimer's Disease in the subject. In one embodiment, the method may further comprise measuring the level of miR-301a, miR-545, or miR-301a and miR-545, in the sample.

In another aspect, the invention provides a method of monitoring the course of Alzheimer's Disease in a subject, by determining the level of at least one miRNA in a first sample containing circulating miRNA from a subject, determining the level of said at least one miRNA in a second sample containing circulating miRNA from said subject, wherein said second sample is obtained after said first sample, and comparing the levels determined in the first sample with levels determined in the second sample, wherein said levels are indicative of Alzheimer's disease progression, and wherein the at least one miRNA is miR-191, miR-15b, miR-142-3p, Let-7g, Let-7d, or combinations thereof. In one embodiment, the method may further comprise measuring the level of miR-301a, miR-545, or miR-301a and miR-545, in the samples.

In another aspect, the invention provides a method of treating Alzheimer's Disease in a subject, by determining the level of at least one miRNA in a sample containing circulating miRNA from said subject, wherein a difference in the level of the at least one miRNA versus that in a normal subject as determined relative to a suitable control is indicative of Alzheimer's Disease in the subject; and, if a difference in the level of at least one miRNA is detected, administering a therapeutically effective amount of a composition comprising an Alzheimer's therapeutic to the subject. In one embodiment, the at least one miRNA is miR-191, miR-15b, miR-142-3p, Let-7g, Let-7d, or combinations thereof. The method may optionally further include determining the level of miR-301a, miR-545, or miR-301a and miR-545, in the sample.

In another aspect, the invention provides a method of treating a subject having Alzheimer's Disease, by identifying a subject having Alzheimer's Disease in which the level of at least one miRNA in a sample containing circulating miRNA from the subject is different (e.g., decreased) relative to a suitable control, and administering a therapeutically effective amount of an Alzheimer's therapeutic to the subject. In one embodiment, the at least one miRNA is miR-191, miR-15b, miR-142-3p, Let-7g, Let-7d, or combinations thereof. The method may optionally include identifying a subject in which the level of miR-301a, miR-545, or miR-301a and miR-545, is also different (e.g., decreased) in the sample relative to a suitable control. In these aspects, the Alzheimer's therapeutic may be Razadyne® (galantamine), Exelon® (rivastigmine), or Aricept® (donepezil). In an exemplary embodiment, the Alzheimer's therapeutic is donepezil or a pharmaceutically acceptable salt or ester thereof (e.g., donepezil hydrochloride).

In another aspect, the invention provides a kit for diagnosing Alzheimer's Disease in a subject, containing an agent that selectively detects the presence of at least one miRNA in a sample containing circulating miRNAs from a subject, wherein the at least one miRNA is miR-191, miR-15b, miR-142-3p, Let-7g, Let-7d, or combinations thereof, and instructions for determining the level of said at least one miRNA, wherein a difference in the level of the at least one miRNA versus that in a normal subject as determined relative to a suitable control is indicative of Alzheimer's Disease in the subject. Such a kit may optionally contain an agent that selectively detects the presence of at least one additional miRNA in the sample, wherein the additional miRNA is miR-301a, miR-545, or miR-301a and miR-545. In some embodiments, the agent specifically hybridizes to a miRNA.

In some embodiments of the methods or kits described herein, the subject may be a mammal, for example, a human.

In methods or kits described herein, the difference in the level of at least one miRNA relative to a suitable control may be determined by executing a software classification algorithm.

In certain embodiments of the methods and kits, the sample may be a bodily fluid, for example, blood, lymph, urine, or saliva. The sample may be a cell-free sample and/or a microvesicle-free sample. In one embodiment, the sample is plasma. In another embodiment, the sample is serum.

In certain embodiments of the methods and kits, wherein one miRNA is selected or used, said miRNA is (a) an miRNA other than miR-191, (b) an miRNA other than miR-15b, (c) an miRNA other than miR-142-3p, (d) an miRNA other than Let-7g, and/or (e) an miRNA other than Let-7d.

In certain embodiments of the methods and kits, wherein the sample is CSF, the miRNA is (a) an miRNA other than miR-15b, and/or (b) an miRNA other than miR-191.

BRIEF DESCRIPTION OF THE DRAWINGS

FIG. 1A and FIG. 1B: Scatter plots of normalized miRNA expression from Cohort 1 (20 Alzheimer's Disease (AD) or Mild Cognitive Impairment (MCI) patients (11 AD; 9 MCI) and 20 Normal Control (NC) patients) using nCounter miRNA assay.

FIG. 2: Scatter plots of linear fold change values, normalized to the average NC values of the individual candidate miRNA biomarkers from Cohort 1 (20 AD or MCI patients and 20 NC patients) using TaqMan RT-qPCR.

FIG. 3: Scatter plots of linear fold change values, normalized to the average control values of the individual candidate miRNA biomarkers from Cohort 2 (20 AD and 17 NC patients) using TaqMan RT-qPCR.

FIG. 4 (Table 1): Available details of patients in Cohort 1, including diagnosis, age, sex, MMSE scores and visit numbers, as obtained from PrecisionMed, Inc.

FIG. 5 (Table 2): Sequence and miRBASE accession numbers of miRNA biomarkers and miRNAs used for normalization.

FIG. 6 (Table 3): Correlation of average fold-change values for candidate miRNA biomarkers between Nanostring and TaqMan platforms for Cohort 1 samples (20 AD or MCI (11 AD; 9 MCI) and 20 NC).

FIG. 7 (Table 4): Relative Ct value data derived from TaqMan qPCR using a subset of Cohort 1 samples (11 AD and 20 NC); data was used to generate signature patterns of candidate miRNA biomarkers to differentiate between AD and NC patients.

FIG. 8 (Table 5): Available details of patients in Cohort 2, including diagnosis, age, sex, MMSE scores and visit numbers, as obtained from PrecisionMed, Inc.

FIG. 9 (Table 6): Correlation of average fold-change values (normalized to average Control values) for candidate miRNA biomarkers between Cohort 1 and Cohort 2 using TaqMan RT-qPCR miRNA assay.

FIG. 10 (Table 7): Relative Ct value data derived from TaqMan qPCR using Cohort 2 samples (20 AD and 17 NC), which was used as input for the algorithm to predict AD and NC patient status using signatures derived from Cohort 1 data (Table 4).

FIG. 11A, FIG. 11B, and FIG. 11C (Table 8A-8C): Candidate miRNA biomarker signatures indicative of Alzheimer's Disease.

FIG. 12A and FIG. 12B (Table 9A-9B): Accuracy, Specificity, Sensitivity and AUC (Area Under the Curve) for miRNA biomarker signatures having an accuracy of >75%.

FIG. 13 (Table 10): Accuracy, Specificity, Sensitivity and AUC (Area Under the Curve) for selected 8 miRNA signature combinations using Cohort 2 samples for prediction.

FIG. 14 (Table 11): Accuracy, Specificity, Sensitivity and AUC (Area under the Curve) for individual miRNAs using Cohort 2 samples for prediction.

DETAILED DESCRIPTION

1. Introduction

The present invention provides novel miRNA biomarkers which are indicative of Alzheimer's Disease, and which may be used to accurately diagnose Alzheimer's Disease in a subject. In addition, methods for monitoring the course of Alzheimer's Disease, methods of treating a subject having Alzheimer's Disease, and kits for diagnosing Alzheimer's Disease are provided. In some embodiments, the methods entail detection of extracellular, circulating miRNAs in a suitable sample, preferably blood, plasma, serum, urine, or saliva.

2. Definitions

Prior to setting forth the invention in detail, definitions of certain terms to be used herein are provided. Unless defined otherwise, all technical and scientific terms used herein have the same meaning as is commonly understood by one of skill in the art.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

The term "subject" is intended to include animals which are capable of suffering from or afflicted with dementia associated with a CNS disorder, including neurodegenerative diseases such as Alzheimer's Disease, or any disorder involving, directly or indirectly, Alzheimer's Disease. Examples of subjects include mammals, e.g., humans, non-human primates, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from Alzheimer's Disease or Alzheimer's Disease-associated dementia.

The term "treat" is used herein to mean to relieve, reduce or alleviate at least one symptom of a disease in a subject. For example, in relation to Alzheimer's Disease, the term "treat" includes relieving, reducing, or alleviating cognitive impairment (such as impairment of memory and/or orientation) or impairment of global functioning (overall functioning, including activities of daily living) and/or slowing down or reversing the progressive deterioration in global or cognitive impairment. Accordingly, the term "treat" also encompasses delaying or preventing onset prior to clinical manifestation of a disease or symptom of a disease and/or reducing the risk of developing or worsening of a symptom of a disease.

A "therapeutically effective amount" of a therapeutic agent, or combinations thereof, is an amount sufficient to treat disease in a subject. For example, for an Alzheimer's therapeutic, a therapeutically effective amount can be an amount that has been shown to provide an observable therapeutic benefit compared to baseline clinically observable signs and symptoms of Alzheimer's disease.

The term "about" or "approximately" usually means within 5%, or more preferably within 1%, of a given value or range.

3. miRNA Biomarkers for Alzheimer's Disease

The invention relates to microRNA ("miRNA") biomarkers found to be differentially present in biological samples derived from subjects having Alzheimer's Disease (AD), as compared with subjects who are "normal," i.e., subjects who do not have Alzheimer's Disease. An miRNA biomarker or set of miRNA biomarkers is differentially present between samples if the difference between the levels of expression of the miRNA biomarker or set of miRNA biomarkers in the samples is determined to be statistically significant. Common tests for statistical significance include, but are not limited to, t-test, ANOVA, Kniskal-Wallis, Wilcoxon, Mann-Whitney, and odds ratio. miRNA biomarkers, alone or in combination, can be used to provide a measure of the relative risk that a subject has or does not have Alzheimer's Disease.

miRNAs are small, non-coding RNAs that are involved in regulating gene expression through different mechanisms, including translational repression. miRNAs are initially transcribed from DNA as lengthy primary miRNA transcripts ("pri-miRNAs"), ranging in size from hundreds to thousands of nucleotides. Pri-miRNA is processed in the nucleus by the enzyme complex Drosha-DGCR8 to form stem-loop precursor miRNA ("pre-miRNA"). Pre-miRNA is transported to the cytoplasm by the protein exportin 5, where it is cleaved by the enzyme Dicer to generate mature (functional) miRNA. The human genome encodes over 1300 miRNAs, which have been cataloged at "miRBase: The microRNA Database" (http://www.mirbase.org/). miRNA expression has been reported in a wide array of cell and tissue types, and extracellularly, e.g., in biological fluids.

miRNA biomarkers of Alzheimer's Disease were discovered by comparing the level of expression of miRNAs in biological samples derived from subjects having Alzheimer's Disease with samples derived from subjects who are "normal," i.e., subjects who do not have AD, and identifying miRNAs that are differentially present. Seven differentially present miRNA biomarkers were identified in this manner, which surprisingly were found to be indicative of Alzheimer's Disease when measured in plasma: miR-191, miR-15b, let-7d, let-7g, miR-142-3p, miR-301a, and miR-545 (see Table 2). These miRNA biomarkers can now be used to determine the Alzheimer's Disease status of a subject, for example, a subject whose Alzheimer's Disease status was previously unknown or who is suspected to be suffering from Alzheimer's disease. This may be accomplished by determining the level of one or more of miR-191, miR-15b, let-7d, let-7g, miR-142-3p, miR-301a, and miR-545, or combinations thereof, in a biological sample derived from the subject. A difference in the level of one or more of these miRNA biomarkers as compared to that in a biological sample derived from a normal subject is an indication that the subject has Alzheimer's Disease.

A subject having a difference in the level of one or more miRNA biomarkers as compared to a normal subject may have Alzheimer's Disease, including early-stage Alzheimer's Disease, moderate or mid-stage Alzheimer's Disease, or severe or late-stage Alzheimer's Disease. In one embodiment, the level of one or more miRNA biomarkers may be used to diagnose Alzheimer's disease in a subject having symptoms characteristic of early-stage Alzheimer's Disease, also known as prodromal Alzheimer's Disease. Subjects having early-stage Alzheimer's Disease typically have MMSE scores of 24-30. Complaints regarding mild memory loss and a declining ability to perform complex tasks are often self-reported or reported by partners and/or caregivers.

In another embodiment, the level of one or more miRNA biomarkers may be used to diagnose Alzheimer's Disease in a subject having symptoms characteristic of "moderately severe cognitive decline," also referred to as "moderate" or "mid-stage" Alzheimer's disease. Moderately severe cognitive decline is characterized by major gaps in memory and the emergence of deficits in cognitive function. At this stage, some assistance with day-to-day activities is indicated.

In another embodiment, the level of one or more miRNA biomarkers may be used to diagnose Alzheimer's Disease in a subject having symptoms characteristic of "severe cognitive decline," also referred to as "moderate" or "mid-stage" Alzheimer's disease. In severe cognitive decline, memory difficulties continue to worsen, significant personality changes may emerge, and affected individuals typically need extensive help with customary daily activities.

In another embodiment, the level of one or more miRNA biomarkers may be used to diagnose Alzheimer's Disease in a subject having symptoms characteristic of "very severe cognitive decline," also referred to as "severe" or "late-stage" Alzheimer's disease. Late stage Alzheimer's disease or very severe cognitive decline is the final stage of the disease. Individuals typically lose the ability to respond to their environment, the ability to speak and, ultimately, the ability to control movement. (See, for example, http://www.alz.org).

In another embodiment, the level of one or more miRNA biomarkers may be used to diagnose Alzheimer's Disease in a subject having an MMSE score between 0 and 26, e.g., an MMSE score of 0-10, an MMSE score of 0-20, an MMSE score of 0-26, etc. "MMSE" refers to the Mini-Mental State Examination used in the cognitive assessment community. During the MMSE, a physician or other medical professional asks a patient a series of questions that are designed to test a range of everyday mental skills Questions commonly asked include, for example, remembering and repeating the names of three common objects, stating the year, date, season, and day of the week, counting backwards from 100 in increments of 7, spelling the word "world" backwards, naming familiar objects as the examiner points to them, identifying the location of the examiner's office, repeating a common phrase after it is stated by the Examiner, copying a picture of two interlocking shapes, and following a three-part series of instructions (e.g., pick up a piece of paper, fold it in half, and place it on the floor). The maximum score on the MMSE examination is 30 points. In general, a patient with an MMSE score of 27-30 is considered to have no cognitive impairment, a patient with an MMSE score of 21-26 is considered to have mild cognitive impairment, a patient with an MMSE score of 11-20 is considered to have moderate cognitive impairment, and a patient with an MMSE score of 0-10 is considered to have severe cognitive impairment. In certain embodiments, a patient with an MMSE score of 0-16 is considered to have advanced (moderately severe to severe) Alzheimer's disease.

In one embodiment, the level of one or more miRNA biomarkers may be used to monitor the course of Alzheimer's Disease in a subject. The Alzheimer's Disease status of a subject can change over time. For example, the disease may worsen or improve over time. With such worsening or improvement, the level of one or more miRNA biomarkers may change, as detected in samples derived from the subject. For example, the level of one or more of miR-191, miR-15b, let-7d, let-7g, miR-142-3p, miR-301a, and/or miR-545 decrease with the development of Alzheimer's Disease. Thus, the course of Alzheimer's Disease in a subject can be monitored by determining the level of one or more miRNA biomarkers in a first sample derived from a subject, and determining the level of one or more miRNA biomarkers in a second sample derived from a subject, where the second sample is obtained after the first sample. The levels in the second sample relative to the levels in the first sample are indicative of disease progression. For example, a decrease in the level of one or more of miR-191, miR-15b, let-7d, let-7g, miR-142-3p, miR-301a, and/or miR-545 from the first sample to the second sample is indicative that the subject has developed Alzheimer's Disease, or that the disease has worsened. Conversely, an increase in the level of one or more of miR-191, miR-15b, let-7d, let-7g, miR-142-3p, miR-301a, and/or miR-545 from the first sample to the second sample indicates that the disease has improved. In one embodiment, the one or more miRNA biomarkers are miR-191, miR-15b, let-7d, let-7g, miR-142-3p, and combinations thereof.

Whether or not the level of a miRNA biomarker in a biological sample derived from a test subject is different from the level of the miRNA biomarker present in a normal subject may be ascertained by comparing the level of the miRNA biomarker in the sample from the test subject with a suitable control. The skilled person can select an appropriate control for the assay in question. For example, a suitable control may be a biological sample derived from a known subject, e.g., a subject known to be a normal subject, or a subject known to have Alzheimer's Disease. If a suitable control is obtained from a normal subject, a statistically significant difference in the level of a miRNA biomarker in a test subject relative to the suitable control is indicative that the subject has Alzheimer's Disease. If a suitable control is obtained from a subject known to have Alzheimer's Disease, levels comparable to or lower than such a control are indicative of Alzheimer's disease, reflective of a difference in the levels present in a sample from a normal subject. In one embodiment, the difference in the level of a miRNA biomarker is a decrease. A suitable control may also be a reference standard. A reference standard serves as a reference level for comparison, such that test samples can be compared to the reference standard in order to infer the Alzheimer's Disease status of a subject. A reference standard may be representative of the level of one or more miRNA biomarkers in a known subject, e.g., a subject known to be a normal subject, or a subject known to have Alzheimer's Disease. Likewise, a reference standard may be representative of the level of one or more miRNA biomarkers in a population of known subjects, e.g., a population of subjects known to be normal subjects, or a population of subjects known to have Alzheimer's Disease. The reference standard may be obtained, for example, by pooling samples from a plurality of individuals and determining the level of a miRNA biomarker in the pooled samples, to thereby produce a standard over an averaged population. Such a reference standard represents an average level of a miRNA biomarker among a population of individuals. A reference standard may also be obtained, for example, by averaging the level of a miRNA biomarker determined to be present in individual samples obtained from a plurality of individuals. Such a standard is also representative of an average level of a miRNA biomarker among a population of individuals. A reference standard may also be a collection of values each representing the level of a miRNA biomarker in a known subject in a population of individuals. In certain embodiments, test samples may be compared against such a collection of values in order to infer the Alzheimer's Disease status of a subject. In certain embodiments, the reference standard is an absolute value. In such embodiments, test samples may be compared against the absolute value in order to infer the Alzheimer's Disease status of a subject. In a one embodiment, a comparison between the level of one or more miRNAs in a sample relative to a suitable control is made by executing a software classification algorithm. The skilled person can readily envision additional suitable controls that may be appropriate depending on the assay in question. The aforementioned suitable controls are exemplary, and are not intended to be limiting.

Generally, a decrease in the level of one or more of miR-191, miR-15b, let-7d, let-7g, miR-142-3p, miR-301a, and/or miR-545 in a biological sample derived from a test subject relative to a suitable control representative of the level of one or more of miR-191, miR-15b, let-7d, let-7g, miR-142-3p, miR-301a, and/or miR-545, respectively in a normal subject will indicate that the test subject has Alzheimer's Disease. In cases where the suitable control is representative of the level of the miRNA biomarkers in a subject having Alzheimer's Disease, generally levels of one or more of miR-191, miR-15b, let-7d, let-7g, miR-142-3p, miR-301a, and/or miR-545 comparable to or lower than those of such a control are indicative of Alzheimer's Disease.

In some instances where the levels of two or more miRNA biomarkers are determined in a test subject, there may be a decrease in the level of one or more miRNA biomarkers, and no change or an increase in the level of one or more additional miRNA biomarkers, relative to a suitable control. In such instances, a difference in the level of one or more of the miRNA biomarkers relative to a suitable control representative of the level of the miRNA biomarkers in a normal subject indicates that the test subject has Alzheimer's Disease. Determination of such a difference may be aided by the execution of a software classification algorithm, as described herein.

4. Biological Samples

The expression level of one or more miRNA biomarkers may be determined in a biological sample derived from a subject. A sample derived from a subject is one that originates from a subject. Such a sample may be further processed after it is obtained from the subject. For example, RNA may be isolated from a sample. In this example, the RNA isolated from the sample is also a sample derived from a subject. A biological sample useful for determining the level of one or more miRNA biomarkers may be obtained from essentially any source, as miRNA expression has been reported in cells, tissues, and fluids throughout the body. However, in one aspect of the invention, levels of one or more biomarkers indicative of Alzheimer's Disease may be detected in a sample obtained from a subject non-invasively. Existing biomarkers for Alzheimer's Disease (e.g., $A\beta_{1-42}$, p-tau, etc.) are often measured in a sample derived from cerebrospinal fluid (CSF) or from brain tissue. CSF is most commonly obtained by lumbar puncture, which is a painful procedure associated with risk factors including bleeding into the spinal canal, spinal headache, and infection. Biomarker detection on samples of brain tissue is currently impractical for diagnosis of Alzheimer's Disease in a living subject, and is used primarily to posthumously confirm a diagnosis made by other means. Accordingly, it is preferred that the sample be obtained from a source other than brain tissue. The miRNA biomarkers described herein are indicative of Alzheimer's Disease and can be detected in biological samples obtained non-invasively.

In a preferred embodiment, the biological sample used for determining the level of one or more miRNA biomarkers is a sample containing circulating miRNAs, e.g., extracellular miRNAs. Extracellular miRNAs freely circulate in a wide range of biological material, including bodily fluids, such as fluids from the circulatory system, e.g., a blood sample or a lymph sample, or from another bodily fluid such as CSF, urine or saliva. Accordingly, in some embodiments, the biological sample used for determining the level of one or more miRNA biomarkers is a bodily fluid, for example, blood, fractions thereof, serum, plasma, urine, saliva, tears, sweat, semen, vaginal secretions, lymph, bronchial secretions, CSF, etc. In some embodiments, the sample is a sample that is obtained non-invasively. In some embodiments, the sample is obtained from a bodily fluid other than CSF.

Circulating miRNAs include miRNAs in cells (cellular miRNA), extracellular miRNAs in microvesicles (microvesicle-associated miRNA), and extracellular miRNAs that are not associated with cells or microvesicles (extracellular, non-vesicular miRNA). In some embodiments, the biological sample used for determining the level of one or more miRNA biomarkers (e.g., a sample containing circulating miRNA) may contain cells. In other embodiments, the biological sample may be free or substantially free of cells (e.g., a serum sample). The sample may likewise be free or substantially free of microvesicles. For example, a sample that is free or substantially free of microvesicles is one in which the microvesicle content of the sample is sufficiently low to avoid interfering with the ability to accurately determine the level of non-vesicular miRNAs in the sample. In some embodiments, a sample containing circulating miRNAs, e.g., extracellular miRNAs, is a blood-derived sample.

Exemplary blood-derived sample types include, e.g., a plasma sample, a serum sample, a blood sample, etc. In other embodiments, a sample containing circulating miRNAs is a lymph sample. Circulating miRNAs are also found in urine and saliva, and biological samples derived from these sources are likewise suitable for determining the level of one or more miRNA biomarkers.

5. Determining the Level of miRNA Biomarkers in a Sample

The level of one or more miRNA biomarkers in a biological sample may be determined by any suitable method. Any reliable method for measuring the level or amount of miRNA in a sample may be used. Generally, miRNA can be detected and quantified from a sample (including fractions thereof), such as samples of isolated RNA by various methods known for mRNA, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoString analysis, Northern Blot analysis, branched DNA (bDNA) signal amplification, in situ hybridization, etc.), and sequencing-based methods (e.g., next-generation sequencing methods, for example, using the Illumina or IonTorrent platforms). Other exemplary techniques include ribonuclease protection assay (RPA) and mass spectroscopy.

In some embodiments, RNA is converted to DNA (cDNA) prior to analysis. cDNA can be generated by reverse transcription of isolated miRNA using conventional techniques. miRNA reverse transcription kits are known and commercially available. Examples of suitable kits include, but are not limited to the mirVana™ TaqMan® miRNA transcription kit (Ambion, Austin, Tex.), and the TaqMan® miRNA transcription kit (Applied Biosystems, Foster City, Calif.). Universal primers, or specific primers, including miRNA-specific stem-loop primers, are known and commercially available, for example, from Applied Biosystems. In some embodiments, miRNA is amplified prior to measurement. In other embodiments, the level of miRNA is measured during the amplification process. In still other embodiments, the level of miRNA is not amplified prior to measurement. Some exemplary methods suitable for determining the level of miRNA in a sample are described in greater detail below. These methods are provided by way of illustration only, and it will be apparent to a skilled person that other suitable methods may likewise be used.

A. Amplification-Based Methods

Many amplification-based methods exist for detecting the level of miRNA nucleic acid sequences, including, but not limited to, PCR, RT-PCR, qPCR, and rolling circle amplification. Other amplification-based techniques include, for example, ligase chain reaction, multiplex ligatable probe amplification, in vitro transcription (IVT), strand displacement amplification, transcription-mediated amplification, RNA (Eberwine) amplification, and other methods that are known to persons skilled in the art.

A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a miRNA) may be performed prior to PCR amplification. Reverse transcription reactions include the use of, e.g., a RNA-based DNA polymerase (reverse transcriptase) and a primer.

Kits for quantitative real time PCR of miRNA are known, and are commercially available. Examples of suitable kits include, but are not limited to, the TaqMan® miRNA Assay (Applied Biosystems) and the mirVana™ qRT-PCR miRNA detection kit (Ambion). The miRNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence.

In some instances, custom qRT-PCR assays can be developed for determination of miRNA levels. Custom qRT-PCR assays to measure miRNAs in a biological sample, e.g., a body fluid, can be developed using, for example, methods that involve an extended reverse transcription primer and locked nucleic acid modified PCR. Custom miRNA assays can be tested by running the assay on a dilution series of chemically synthesized miRNA corresponding to the target sequence. This permits determination of the limit of detection and linear range of quantitation of each assay. Furthermore, when used as a standard curve, these data permit an estimate of the absolute abundance of miRNAs measured in biological samples.

Amplification curves may optionally be checked to verify that Ct values are assessed in the linear range of each amplification plot. Typically, the linear range spans several orders of magnitude. For each candidate miRNA assayed, a chemically synthesized version of the miRNA can be obtained and analyzed in a dilution series to determine the limit of sensitivity of the assay, and the linear range of quantitation. Relative expression levels may be determined, for example, according to the 2(−ΔΔ C(T)) Method, as described by Livak et al., Analysis of relative gene expression data using real-time quantitative PCR and the 2(−ΔΔ C(T)) Method. *Methods* (2001) December; 25(4):402-8.

In some embodiments, two or more miRNAs are amplified in a single reaction volume. For example, multiplex q-PCR, such as qRT-PCR, enables simultaneous amplification and quantification of at least two miRNAs of interest in one reaction volume by using more than one pair of primers and/or more than one probe. The primer pairs comprise at least one amplification primer that specifically binds each miRNA, and the probes are labeled such that they are distinguishable from one another, thus allowing simultaneous quantification of multiple miRNAs.

Rolling circle amplification is a DNA-polymerase driven reaction that can replicate circularized oligonucleotide probes with either linear or geometric kinetics under isothermal conditions (see, for example, Lizardi et al., Nat. Gen. (1998) 19(3):225-232; Gusev et al., Am. J. Pathol. (2001) 159(1):63-69; Nallur et al., Nucleic Acids Res. (2001) 29(23):E118). In the presence of two primers, one hybridizing to the (+) strand of DNA, and the other hybridizing to the (−) strand, a complex pattern of strand displacement results in the generation of over $10^9$ copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of miRNA sequence and expression level at very low miRNA concentrations (see, for example, Cheng et al., Angew Chem. Int. Ed. Engl. (2009) 48(18):3268-72; Neubacher et al., Chembiochem. (2009) 10(8):1289-91).

B. Hybridization-Based Methods miRNA may be detected using hybridization-based methods, including but not limited to hybridization arrays (e.g., microarrays), NanoString analysis, Northern Blot analysis, branched DNA (bDNA) signal amplification, and in situ hybridization.

Microarrays can be used to measure the expression levels of large numbers of miRNAs simultaneously. Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays. Also useful are microfluidic TaqMan Low-Density Arrays, which are based on an array of microfluidic qRT-PCR reactions, as well as related microfluidic qRT-PCR based methods.

In one example of microarray detection, various oligonucleotides (e.g., 200+5'-amino-modified-C6 oligos) corresponding to human sense miRNA sequences are spotted on three-dimensional CodeLink slides (GE Health/Amersham Biosciences) at a final concentration of about 20 μM and processed according to manufacturer's recommendations. First strand cDNA synthesized from 20 μg TRIzol-purified total RNA is labeled with biotinylated ddUTP using the Enzo BioArray end labeling kit (Enzo Life Sciences Inc.). Hybridization, staining, and washing can be performed according to a modified Affymetrix Antisense genome array protocol.

Axon B-4000 scanner and Gene-Pix Pro 4.0 software or other suitable software can be used to scan images. Non-positive spots after background subtraction, and outliers detected by the ESD procedure, are removed. The resulting signal intensity values are normalized to per-chip median values and then used to obtain geometric means and standard errors for each miRNA. Each miRNA signal can be transformed to log base 2, and a one-sample t test can be conducted. Independent hybridizations for each sample can be performed on chips with each miRNA spotted multiple times to increase the robustness of the data.

Microarrays can be used for the expression profiling of miRNAs in diseases. For example, RNA can be extracted from a sample and, optionally, the miRNAs are size-selected from total RNA. Oligonucleotide linkers can be attached to the 5' and 3' ends of the miRNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the, capture probes are affixed. The spot will then fluoresce when excited using a microarray laser scanner.

The fluorescence intensity of each spot is then evaluated in terms of the number of copies of a particular miRNA, using a number of positive and negative controls and array data normalization methods, which will result in assessment of the level of expression of a particular miRNA.

Total RNA containing the miRNA extracted from a body fluid sample can also be used directly without size-selection of the miRNAs. For example, the RNA can be 3' end labeled using T4 RNA ligase and a fluorophore-labeled short RNA linker. Fluorophore-labeled miRNAs complementary to the corresponding miRNA capture probe sequences on the array hybridize, via base pairing, to the spot at which the capture probes are affixed. The fluorescence intensity of each spot is then evaluated in terms of the number of copies of a particular miRNA, using a number of positive and negative controls and array data normalization methods, which will result in assessment of the level of expression of a particular miRNA.

Several types of microarrays can be employed including, but not limited to, spotted oligonucleotide microarrays, pre-fabricated oligonucleotide microarrays or spotted long oligonucleotide arrays.

miRNAs can also be detected without amplification using the nCounter Analysis System (NanoString Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter miRNA assay kits are available from NanoString Technologies, which are capable of distinguishing between highly similar miRNAs with great specificity.

miRNAs can also be detected using branched DNA (bDNA) signal amplification (see, for example, Urdea, Nature Biotechnology (1994), 12:926-928). miRNA assays based on bDNA signal amplification are commercially available. One such assay is the QuantiGene® 2.0 miRNA Assay (Affymetrix, Santa Clara, Calif.).

Northern Blot and in situ hybridization may also be used to detect miRNAs. Suitable methods for performing Northern Blot and in situ hybridization are known in the art.

C. Sequencing-Based Methods

Advanced sequencing methods can likewise be used as available. For example, miRNAs can be detected using Illumina® Next Generation Sequencing (e.g., Sequencing-By-Synthesis or TruSeq methods, using, for example, the HiSeq, HiScan, GenomeAnalyzer, or MiSeq systems (Illumina, Inc., San Diego, Calif.)). miRNAs can also be detected using Ion Torrent Sequencing (Ion Torrent Systems, Inc., Gulliford, Conn.), or other suitable methods of semiconductor sequencing.

D. Additional miRNA Detection Tools

Mass spectroscopy can be used to quantify miRNA using RNase mapping. Isolated RNAs can be enzymatically digested with RNA endonucleases (RNases) having high specificity (e.g., RNase Tl, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESI-MS. The presence of posttranscriptional modifications can be revealed by mass shifts from those expected based upon the RNA sequence. Ions of anomalous mass/charge values can then be isolated for tandem MS sequencing to locate the sequence placement of the post-transcriptionally modified nucleoside.

Matrix-assisted laser desorption/ionization mass spectrometry (MALDI-MS) has also been used as an analytical approach for obtaining information about posttranscriptionally modified nucleosides. MALDI-based approaches can be differentiated from ESI-based approaches by the separation step. In MALDI-MS, the mass spectrometer is used to separate the miRNA.

To analyze a limited quantity of intact miRNAs, a system of capillary LC coupled with nanoESI-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR® XL, Applied Biosystems) equipped with a custom-made nanospray ion source, a Nanovolume Valve (Valco Instruments), and a splitless nano HPLC system (DiNa, KYA Technologies). Analyte/TEAA is loaded onto a nano-LC trap column, desalted, and then concentrated. Intact miRNAs are eluted from the trap column and directly injected into a Cl 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for miRNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. Multiple miRNAs can be detected in a microarray format using a novel approach that combines a surface enzyme reaction with nanoparticle-amplified SPR imaging (SPRI). The surface reaction of poly(A) polymerase creates poly(A) tails on miRNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for miRNA profiling at attamole levels.

E. Detection of Amplified or Non-Amplified miRNAs

In certain embodiments, labels, dyes, or labeled probes and/or primers are used to detect amplified or unamplified miRNAs. The skilled artisan will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where miRNA amplification is preferred.

A probe or primer may include standard (A, T or U, G and C) bases, or modified bases. Modified bases include, but are not limited to, the AEGIS bases (from Eragen Biosciences), which have been described, e.g., in U.S. Pat. Nos. 5,432,272, 5,965,364, and 6,001,983. In certain aspects, bases are joined by a natural phosphodiester bond or a different chemical linkage. Different chemical linkages include, but are not limited to, a peptide bond or a Locked Nucleic Acid (LNA) linkage, which is described, e.g., in U.S. Pat. No. 7,060,809.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan™) probes (see U.S. Pat. No. 5,538,848), stem-loop molecular beacons (see, e.g., U.S. Pat. Nos. 6,103,476 and 5,925,517), stemless or linear beacons (see, e.g., WO 9921881, U.S. Pat. Nos. 6,485,901 and 6,649,349), peptide nucleic acid (PNA) Molecular Beacons (see, e.g., U.S. Pat. Nos. 6,355,421 and 6,593,091), linear PNA beacons (see, e.g. U.S. Pat. No. 6,329,144), non-FRET probes (see, e.g., U.S. Pat. No. 6,150,097), Sunrise™/AmplifluorB™ probes (see, e.g., U.S. Pat. No. 6,548,250), stem-loop and duplex Scorpion™ probes (see, e.g., U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB Eclipse™ probe (Epoch Biosciences), hairpin probes (see, e.g., U.S. Pat. No. 6,596,490), PNA light-up probes, antiprimer quench probes (Li et al., Clin. Chem. 53:624-633 (2006)), self-assembled nanoparticle probes, and ferrocene-modified probes described, for example, in U.S. Pat. No. 6,485,901.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels.

In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g., biotin-avidin). In still other aspects, use of labels can be accomplished using any one of a large number of known techniques employing known labels, linkages, linking groups, reagents, reaction conditions, and analysis and purification methods.

miRNAs can be detected by direct or indirect methods. In a direct detection method, one or more miRNAs are detected by a detectable label that is linked to a nucleic acid molecule. In such methods, the miRNAs may be labeled prior to binding to the probe. Therefore, binding is detected by screening for the labeled miRNA that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified miRNAs, are detected using FlexMAP Microspheres (Luminex) conjugated with probes to capture the desired nucleic acids. Some methods may involve detection with polynucleotide probes modified with fluorescent labels or branched DNA (bDNA) detection, for example.

In other embodiments, nucleic acids are detected by indirect detection methods. For example, a biotinylated probe may be combined with a streptavidin-conjugated dye to detect the bound nucleic acid. The streptavidin molecule binds a biotin label on amplified miRNA, and the bound miRNA is detected by detecting the dye molecule attached to the streptavidin molecule. In one embodiment, the streptavidin-conjugated dye molecule comprises Phycolink® Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal (see, e.g., Kricka, L., Nonisotopic DNA Probe Techniques, Academic Press, San Diego (1992) and Garman A., Non-Radioactive Labeling, Academic Press (1997).). A dual labeled fluorescent probe that includes a reporter fluorophore and a quencher fluorophore is used in some embodiments. It will be appreciated that pairs of fluorophores are chosen that have distinct emission spectra so that they can be easily distinguished.

In certain embodiments, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g., Blackburn et al., eds. "DNA and RNA Structure" in Nucleic Acids in Chemistry and Biology (1996)).

In other embodiments, methods relying on hybridization and/or ligation to quantify miRNAs may be used, including oligonucleotide ligation (OLA) methods and methods that allow a distinguishable probe that hybridizes to the target nucleic acid sequence to be separated from an unbound probe. As an example, HARP-like probes, as disclosed in U.S. Publication No. 2006/0078894 may be used to measure the quantity of miRNAs. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

A probe ligation reaction may also be used to quantify miRNAs. In a Multiplex Ligation-dependent Probe Amplification (MLPA) technique (Schouten et al., *Nucleic Acids Research* 30:e57 (2002)), pairs of probes which hybridize immediately adjacent to each other on the target nucleic acid are ligated to each other driven by the presence of the target nucleic acid. In some aspects, MLPA probes have flanking PCR primer binding sites. MLPA probes are specifically amplified when ligated, thus allowing for detection and quantification of miRNA biomarkers.

6. Determination of Alzheimer's Disease Status Using miRNA Biomarkers

The miRNA biomarkers described herein can be used individually or in combination in diagnostic tests to assess the Alzheimer's Disease status of a subject. Disease status includes the presence or absence of Alzheimer's Disease. Disease status may also include monitoring the course of Alzheimer's Disease, for example, monitoring disease progression. Based on the Alzheimer's Disease status of a subject, additional procedures may be indicated, including, for example, additional diagnostic tests or therapeutic procedures.

The power of a diagnostic test to correctly predict disease status is commonly measured in terms of the accuracy of the assay, the sensitivity of the assay, the specificity of the assay, or the "Area Under a Curve" (AUC), for example, the area under a Receiver Operating Characteristic (ROC) curve. As used herein, accuracy is a measure of the fraction of misclassified samples. Accuracy may be calculated as the total number of correctly classified samples divided by the total number of samples, e.g., in a test population. Sensitivity is a measure of the "true positives" that are predicted by a test to be positive, and may be calculated as the number of correctly identified Alzheimer's Disease samples divided by the total number of Alzheimer's Disease samples. Specificity is a measure of the "true negatives" that are predicted by a test to be negative, and may be calculated as the number of correctly identified normal samples divided by the total number of normal samples. AUC is a measure of the area under a Receiver Operating Characteristic curve, which is a plot of sensitivity vs. the false positive rate (1-specificity). The greater the AUC, the more powerful the predictive value of the test. Other useful measures of the utility of a test include the "positive predictive value," which is the percentage of actual positives who test as positives, and the "negative predictive value," which is the percentage of actual negatives who test as negatives. In a preferred embodiment, the level of one or more miRNA biomarkers in samples derived from subjects having different Alzheimer's Disease statuses show a statistically significant difference of at least $p \leq 0.05$, e.g., $p \leq 0.05$, $p \leq 0.01$, $p \leq 0.005$, $p \leq 0.001$, etc. relative to normal subjects, as determined relative to a suitable control. In other preferred embodiments, diagnostic tests that use miRNA biomarkers described herein individually or in combination show an accuracy of at least about 75%, e.g., an accuracy of at least about 75%, about 80%, about 85%, about 90%, about 95%, about 97%, about 99% or about 100%. In other embodiments, diagnostic tests that use miRNA biomarkers described herein individually or in combination show a specificity of at least about 75%, e.g., a specificity of at least about 75%, about 80%, about 85%, about 90%, about 95%, about 97%, about 99% or about 100%. In other embodiments, diagnostic tests that use miRNA biomarkers described herein individually or in combination show a sensitivity of at least about 75%, e.g., a sensitivity of at least about 75%, about 80%, about 85%, about 90%, about 95%, about 97%, about 99% or about 100%. In other embodiments, diagnostic tests that use miRNA biomarkers described herein individually or in combination show a specificity and sensitivity of at least about 75% each, e.g., a specificity and sensitivity of at least about 75%, about 80%, about 85%, about 90%, about 95%, about 97%, about 99% or about 100% (for example, a specificity of at least about 80% and sensitivity of at least about 80%, or for example, a specificity of at least about 80% and sensitivity of at least about 95%).

Each biomarker listed in Table 2 is differentially present in biological samples derived from subjects having Alzheimer's Disease as compared with normal subjects, and thus each is individually useful in facilitating the determination of Alzheimer's Disease in a test subject. Such a method involves determining the level of the biomarker in a sample derived from the subject. Determining the level of the biomarker in a sample may include measuring, detecting, or assaying the level of the biomarker in the sample using any suitable method, for example, the methods set forth herein. Determining the level of the biomarker in a sample may also include examining the results of an assay that measured, detected, or assayed the level of the biomarker in the sample. The method may also involve comparing the level of the biomarker in a sample with a suitable control. A change in the level of the biomarker relative to that in a normal subject as assessed using a suitable control is indicative of the Alzheimer's Disease status of the subject. A diagnostic amount of a biomarker that represents an amount of the biomarker above or below which a subject is classified as having a particular Alzheimer's Disease status can be used. For example, if the biomarker is downregulated in samples derived from an individual having Alzheimer's Disease as compared to a normal individual, a measured amount below the diagnostic cutoff provides a diagnosis of Alzheimer's Disease. Generally, the individual miRNA biomarkers in Table 2 are downregulated in Alzheimer's Disease samples relative to samples obtained from normal individuals. As is well-understood in the art, adjusting the particular diagnostic cut-off used in an assay allows one to adjust the sensitivity and/or specificity of the diagnostic assay as desired. The particular diagnostic cut-off can be determined, for example, by measuring the amount of the biomarker in a statistically significant number of samples from subjects with different Alzheimer's Disease statuses, and drawing the cut-off at the desired level of accuracy, sensitivity, and/or specificity. In certain embodiments, the diagnostic cut-off can be determined with the assistance of a classification algorithm, as described herein.

Accordingly, methods are provided for diagnosing Alzheimer's Disease in a subject, by determining the level of at least one miRNA in a sample containing circulating miRNA from the subject, wherein a difference in the level of the at least one miRNA versus that in a normal subject (as determined relative to a suitable control) is indicative of Alzheimer's Disease in the subject. The at least one miRNA preferably includes one or more of miR-191, miR-15b, miR-142-3p, Let-7g, and Let-7d, and may optionally include miR-301a, miR-545, or miR-301a and miR-545. For example, the present invention provides a method of determining the level of at least one miRNA in a sample containing circulating miRNA derived from the subject, wherein a decrease in the level of the at least one miRNA relative to a control is indicative of Alzheimer's Disease in the subject.

Optionally, the method may further comprise providing a diagnosis that the subject has or does not have Alzheimer's Disease based on the level of at least one miRNA in the sample. In addition or alternatively, the method may further comprise correlating a difference in the level or levels of at least one miRNA relative to a suitable control with a diagnosis of Alzheimer's Disease in the subject. In some embodiments, such a diagnosis may be provided directly to the subject, or it may be provided to another party involved in the subject's care.

While individual miRNA biomarkers are useful in diagnostic applications for Alzheimer's Disease, as shown herein, a combination of miRNA biomarkers may provide greater predictive value of Alzheimer's Disease status than the miRNA biomarkers when used alone. Specifically, the detection of a plurality of miRNA biomarkers can increase the accuracy, sensitivity, and/or specificity of a diagnostic test. Exemplary miRNA biomarkers and biomarker combinations are shown in Table 8A-8C. miRNA biomarkers and biomarker combinations demonstrating an overall accuracy of 75% are shown in Table 9A-9B. The invention includes the individual biomarkers and biomarker combinations as set forth in these tables, and their use in methods and kits described herein.

Accordingly, methods are provided for diagnosing Alzheimer's Disease in a subject, by determining the level of two or more miRNAs in a sample containing circulating miRNA from the subject, wherein a difference in the level of the miRNAs versus that in a normal subject (as determined relative to a suitable control) is indicative of Alzheimer's Disease in the subject. The miRNAs preferably include one or more of miR-191, miR-15b, miR-142-3p, Let-7g, and Let-7d, and may optionally include miR-301a, miR-545, or miR-301a and miR-545. Exemplary combinations of two or more miRNA biomarkers include, for example, miR-545, let7g, and miR-15b; miR-15b and miR-545; miR-301a, miR-545, let-7g and miR-15b; miR-191 and miR-15b; Let-7g and miR-15b; miR-191, miR-301a, and miR-545; miR-301a, let-7g, and miR-15b; and miR-191, miR-301a, miR-545, and miR-15b.

Also provided is a method of diagnosing Alzheimer's Disease in a subject by determining the levels of two or more miRNAs in a sample containing circulating miRNA from the subject, comparing the levels of the two or more miRNAs in the sample to a set of data representing levels of the same miRNAs present in normal subjects and subjects having Alzheimer's Disease, and diagnosing the subject as having or not having Alzheimer's Disease based on the comparison. In such a method, the set of data serves as a suitable control or reference standard for comparison with the sample from the subject. Comparison of the sample from the subject with the set of data may be assisted by a classification algorithm, which computes whether or not a statistically significant difference exists between the collective levels of the two or more miRNAs in the sample, and the levels of the same miRNAs present in normal subjects or subjects having Alzheimer's Disease.

7. Generation of Classification Algorithms for Qualifying Alzheimer's Disease Status In some embodiments, data that are generated using samples such as "known samples" can then be used to "train" a classification model. A "known sample" is a sample that has been pre-classified, e.g., classified as being derived from a normal subject, or from a subject having Alzheimer's Disease. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

In some embodiments, data for the training data set that is used to form the classification model can be obtained directly from quantitative PCR (for example, Ct values obtained using the $\Delta\Delta Ct$ method), or from high-throughput expression profiling, such as microarray analysis (for example, total counts or normalized counts from a miRNA expression assay, e.g., the nCounter miRNA expression assay).

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm. Learning algorithms asserted for use in classifying biological information are described, for example, in PCT International Publication No. WO 01/31580 (Barnhill et al., "Methods and devices for identifying patterns in biological systems and methods of use thereof"), U.S. patent application No. 2002 0193950 A1 (Gavin et al, "Method or analyzing mass spectra"), U.S. patent application No. 2003 0004402 A1 (Hitt et al., "Process for discriminating between biological states based on hidden patterns from biological data"), and U.S. patent application No. 2003 0055615 A1 (Zhang and Zhang, "Systems and methods for processing biological expression data"). The contents of the foregoing patent applications are incorporated herein by reference in their entirety.

The classification models can be formed on and used on any suitable digital computer. Suitable digital computers include micro, mini, or large computers using any standard or specialized operating system, such as a Unix, Windows™ or Linux™ based operating system.

The training data set(s) and the classification models can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above can be used for developing classification algorithms for miRNA biomarkers for Alzheimer's disease. The classification algorithms can, in turn, be used in diagnostic tests by providing diagnostic values (e.g., cut-off points) for biomarkers used singly or in combination.

8. Additional Diagnostic Tests

The level of miRNA biomarkers indicative of Alzheimer's Disease may be used as a stand-alone diagnostic indicator of Alzheimer's Disease in a subject. Optionally, the methods may include the performance of at least one additional test to facilitate the diagnosis of Alzheimer's Disease. For example, other tests in addition to determining the level of one or more miRNA biomarkers in order to facilitate a diagnosis of Alzheimer's Disease may be performed. Any other test or combination of tests used in clinical practice to facilitate a diagnosis of Alzheimer's Disease may be used in conjunction with the miRNA biomarkers described herein.

For example, a clinician may perform mental status tests on a subject, in addition to determining the level of one or more miRNA biomarkers in a sample derived from the subject. Such tests may include, but are not limited to, the mini-mental state examination (MMSE), the mini-cog test, the ADAS-cog test, and/or a clock-drawing test. These tests are routinely used in clinical practice to facilitate a diagnosis of Alzheimer's Disease.

Likewise, brain imaging tests may be performed on the subject, for example, an MRI or a CT scan. These tests are performed primarily to rule out other conditions that may cause symptoms similar to Alzheimer's Disease, such as tumors, strokes, or fluid in the brain.

A neurological exam may be performed on the subject, in which conditions such as the subject's reflexes, coordination, muscle strength, eye movement, speech, and/or sensation are tested.

The subject may also be screened for genetic factors indicating that a subject may have a heightened risk for developing Alzheimer's Disease. The subject may likewise be screened for the presence, absence, or level of at least one other biomarker indicative of Alzheimer's Disease.

9. Methods of Treatment

In some embodiments, where a subject is diagnosed with Alzheimer's Disease by the methods described herein, the present invention further provides methods of treating such subjects identified to have Alzheimer's Disease. Accordingly, in one embodiment, the invention relates to a method of treating Alzheimer's Disease in a subject, comprising determining the level of at least one miRNA biomarker in a sample derived from the subject, wherein a difference in the level of at least one miRNA biomarker versus that in a normal subject as determined relative to a suitable control is indicative of Alzheimer's Disease in the subject, and administering a therapeutically effective amount of an Alzheimer's therapeutic to the subject. In another embodiment, the invention relates to a method of treating a subject having Alzheimer's Disease, comprising identifying a subject having Alzheimer's Disease in which the level of at least one miRNA biomarker in a sample derived from the subject is different (e.g., decreased) versus that in a normal subject as determined relative to a suitable control, and administering a therapeutically effective amount of an Alzheimer's therapeutic to the subject.

The term "Alzheimer's therapeutic" includes, for example, substances approved by the U.S. Food and Drug Administration for the treatment of Alzheimer's Disease. Such substances include, for example, Razadyne® (galantamine), Exelon® (rivastigmine), and Aricept® (donepezil). In an exemplary embodiment, the Alzheimer's therapeutic is donepezil or a pharmaceutically acceptable salt or ester thereof (e.g., donepezil hydrochloride).

The Alzheimer's therapeutics may be administered to a subject using a pharmaceutical composition. Suitable pharmaceutical compositions comprise an Alzheimer's therapeutic (or a pharmaceutically acceptable salt or ester thereof), and optionally comprise a pharmaceutically acceptable carrier, such as a pharmaceutical composition comprising galantamine, rivastigmine, donepezil or a pharmaceutically acceptable salt or ester of any of the foregoing (e.g., galantamine hydrobromide, rivastigmine tartrate, donepezil hydrochloride). In certain embodiments, these compositions optionally further comprise one or more additional therapeutic agents.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent. For example, a free base function can be reacted with a suitable acid. Furthermore, where the compounds carry an acidic moiety, suitable pharmaceutically acceptable salts thereof may, include metal salts such as alkali metal salts, e.g. sodium or potassium salts; and alkaline earth metal salts, e.g. calcium or magnesium salts.

The term "pharmaceutically acceptable ester", as used herein, refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms.

As described above, the pharmaceutical compositions may additionally comprise a pharmaceutically acceptable carrier. The term carrier includes any and all solvents, diluents, or other liquid vehicle, dispersion or suspension aids, surface active agents, isotonic agents, thickening or emulsifying agents, preservatives, solid binders, lubricants and the like, suitable for preparing the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Compositions for use in the present invention may be formulated to have any concentration of the Alzheimer's therapeutic desired. In preferred embodiments, the composition is formulated such that it comprises a therapeutically effective amount of the Alzheimer's therapeutic.

10. Kits for Detecting miRNA Biomarkers

In another aspect, the present invention provides kits for diagnosing Alzheimer's Disease status in a subject, which kits are useful for determining the level of one or more of miR-191, miR-15b, let-7d, let-7g, miR-142-3p, miR-301a, and miR-545, and combinations thereof. In one embodiment, the one or more miRNAs are selected from the group consisting of miR-191, miR-15b, let-7d, let-7g, miR-142-3p. Kits may include materials and reagents adapted to selectively detect the presence of a miRNA or group of miRNAs diagnostic for Alzheimer's Disease in a sample derived from a subject. For example, in one embodiment, the kit may include a reagent that specifically hybridizes to a miRNA. Such a reagent may be a nucleic acid molecule in a form suitable for detecting the miRNA, for example, a probe or a primer. The kit may include reagents useful for performing an assay to detect one or more miRNAs, for example, reagents which may be used to detect one or more miRNAs in a qPCR reaction. The kit may likewise include a microarray useful for detecting one or more miRNAs.

In a further embodiment, the kit may contain instructions for suitable operational parameters in the form of a label or product insert. For example, the instructions may include information or directions regarding how to collect a sample, how to determine the level of one or more miRNA biomarkers in a sample, or how to correlate the level of one or more miRNA biomarkers in a sample with the Alzheimer's Disease status of a subject.

In another embodiment, the kit can contain one or more containers with miRNA biomarker samples, to be used as reference standards, suitable controls, or for calibration of an assay to detect the miRNA biomarkers in a test sample.

The invention is further illustrated by the following examples, which should not be construed as limiting. The entire contents of all references, patents and published patent applications cited throughout this application are hereby incorporated by reference in their entirety.

EXAMPLES

Example 1: Identification and Validation of Candidate miRNA Biomarkers

The aim of this study was to generate miRNA profiles from the plasma fraction of human blood, and determine if there are significant differences in miRNA content and expression level between patients diagnosed with Alzheimer's (AD) and normal controls (NC).

Human plasma samples were purchased from PrecisionMed, Inc. (Solano Beach, Calif.-USA). Cohort 1 contained samples from 11 AD patients, 9 Mild Cognitive Impairment (MCI) patients, and 20 NC patients. Age, sex, diagnosis, and mini-mental state examination (MMSE) scores for patients in Cohort 1 are provided in Table 1. Total RNA was extracted from plasma samples (1 mL), and spike-in synthetic miRNAs (Ath-159a and Neg-A) were added to control for extraction efficiency and normalization, as described below.

Each sample was then used for high-throughput expression profiling using the nCounter miRNA expression assay (Nanostring Technology, Seattle, Wash.-USA) in triplicate, as described below. Post normalization and back-ground correction, final linear counts were averaged for both AD/MCI and NC samples, and fold change values were determined. Candidate miRNAs were chosen which had at least a 1.5 fold difference between average expression values in AD/MCI and NC samples, and which had average normalized counts >200. miRNA 106a (Hsa-miR-106a) was identified as a potential endogenous control which showed minimum variation across all AD/MCI and NC samples.

There were 227 miRNAs identified which at least had an average expression count >100 (considered significantly expressed over background). Of the 227 miRNAs, we identified 13 miRNAs which had at least a 1.5 fold difference, and had an average of >200 normalized linear counts (FIGS. 1A and 1B). These included hsa-let-7d, hsa-let-7g, hsa-miR-15b, hsa-miR-126, hsa-miR-142-3p, hsa-miR-191, hsa-miR-301a, hsa-miR-453, hsa-miR-545, hsa-miR-563, hsa-miR-600, hsa-miR-1274a and hsa-miR-1975.

Candidate miRNA biomarkers identified using the high-throughput Nanostring platform were then validated using the stem-loop TaqMan RT-qPCR miRNA assay (Life Technologies). A 1:10 dilution of total RNA for all 40 Cohort 1 samples was made, and the TaqMan assay was performed on each sample as described below. Ath-159a (spike-in) and miR-106a (endogenous miRNA) values were used to normalize values across all samples using the ΔΔCt method of analysis (Life Technologies). Of the 13 miRNAs tested, the presence of 6 miRNAs could not be confirmed. These included hsa-miR-126, hsa-miR-453, hsa-miR-563, hsa-miR-600, hsa-miR-1274a and hsa-miR-1975.

The remaining 7 miRNAs (miR-191, miR-15b, let-7d, let-7g, miR-142-3p, miR-301a and miR-545) showed very strong correlation between the average fold changes recorded by Nanostring and by TaqMan (FIG. 2, Table 3). miRNA sequences and miRBase accession numbers are provided in Table 2. For example, miR-191 was down-regulated in AD samples by ~3.1 fold according to Nanostring analysis, while it was found to be down-regulated ~3.7 fold by TaqMan analysis (see Table 3). This close trend was observed across all remaining miRNAs (miR-15b, let-7d, let-7g, miR-142-3p, miR-301a and miR-545). All fold change values had a p-value <0.005.

It is noteworthy that all the candidate miRNAs (except miR-126) which could not be confirmed by TaqMan analysis had normalized linear counts (as determined by Nanostring) of less than 500. The average counts of each of the validated miRNAs on the other hand were higher than 3,000. This suggests setting a higher threshold for Nanostring experiments may be useful to lessen the number of false-positive candidates.

Materials and Methods
Total RNA Extraction

Total RNA was extracted using a modified miRvana PARIS protocol (Life Technologies; AM 1556) as described (Mitchell, P. S. et al. PNAS. 2008 Jul. 29; 105(30):10513-8). 1 mL of human plasma was added to an equal amount of 2× denaturing buffer and then spiked with 10 µl of 0.05 µM Ath-159a and 40 µM of Neg-A (UUGUGGCGAGCG-GAAUGGAAU) (synthetic miRNAs used for normalization and extraction efficiency Control). Phenol extraction was performed twice, and total RNA was finally eluted in 70 µl of water following protocol recommendation (AM1556).

High-Throughput Expression Profiling of miRNAs

45 µl of purified total RNA was concentrated down to 9 µl and used as template for the nCounter miRNA expression assay (Nanostring Technology, Seattle, Wash.-USA). The sample preparation was set up as recommended (Nanostring; C-0009-02) using 3 µl of concentrated total RNA as the starting amount for all samples in triplicate. Since the amount of total RNA recovered was not enough to be reliably detected using standard spectra-based instruments such as the Nanodrop, an equal volume approach was adopted in which 3 µl of concentrated total RNA was used as starting material for all Nanostring based assays (also utilized in Mitchell, P. S. et al. PNAS. 2008 Jul. 29; 105(30):10513-8). The reactions were set up for an overnight hybridization for 16 hours at 65° C. The next day, the samples were processed through the nCounter Prep Station (Nanostring Technology, Seattle, Wash.-USA, v. 20081003) as recommended by the manufacturer's protocol, followed by processing through the nCounter Digital Analyzer (Nanostring Technology, Seattle, Wash.-USA, v. 20081009). The analyzer resolution was set at 600 FOVs. Data was downloaded and analyzed on Excel as recommended (nCounter Data Analysis guidelines). Briefly, the data was first normalized for lane to lane variation using the provided positive assay controls. This was followed by a global mean normalization by using the counts of the highest 100 miRNA expressers. Each normalized value was then checked to ensure that it was at least 2 SDs higher than the average of background signal recorded for that lane. Any value below that was converted to zero. Fold change values were calculated by taking the average of all AD/MCI and NC sample expression values for individual miRNAs.

Validation of Candidate Biomarker miRNAs Using TaqMan qPCR

Candidate miRNA biomarkers identified using the high-throughput Nanostring platform were then validated by using the stem-loop TaqMan RT-qPCR miRNA assay (Life Technologies). Briefly, a RT primer pool was created with specific miRNA RT primers (miR-301a, miR-1975, miR-191, miR-15b, miR-126, let-7g, let-7d, miR-545, miR-1274, miR-142-3p, miR-600, miR-453, miR-563, miR-106a and ath-159a) at a final concentration of 0.05× in 1×TE. miRNA-specific primers and probes were purchased from Life Technologies. A 15 µl RT reaction was set up containing 6 µl of the RT primer pool, 0.3 µL dNTPS (100 mM), 3 µl of Multiscribe RT (50 U/µl), 1.5 µl of the 10× Reverse Transcription buffer and 0.2 µl of RNAseIN (20 U/µl) and water. All Reverse Transcription components were contained in the miRNA RT kit (Life Technologies; #4366596). Three µl of total RNA (1:10 dilution) was added as template for each sample and the reaction was incubated on ice for 5 min followed by 30 min at 16° C., 30 min at 42° C., and 5 min at 85° C. for enzyme inactivation. The reaction was then stored at 4° C. A second pool of pre-amplification primers was then created with each PCR primer probe (20×) for the same assays mixed at a final concentration of 0.2× in 1×TE. A pre-amplification reaction was set up containing 2× Pre-amplification master mix (Life Technologies; #4391128), 3.75 µl of the custom pre-amplification primer pool and water (making up the reaction volume to 22.5 µl). 2.5 µl of the RT product was then added and cycled through the pre-amplification program [95° C. for 10 min, 55° C. for 2 min, and 72° C. for 2 min followed by 12 cycles of 95° C. for 15 sec and 60° C. for 4 min]. This was followed by a 99.9° C. incubation for 10 min, and then the reaction was diluted by adding 175 µl of 0.1×TE (pH 8.0) and mixed by inversion. Two µl of the pre-amplification product was then used for individual standard TaqMan qPCR reactions (in duplicate) following standard protocol (Life Technologies; P/N 4364031-Rev D) on an ABI7500 instrument. Ct values were calculated by setting a manual threshold of 0.2 and an automatic baseline for all the reactions in a single study (SDS 2.4, Life Technologies) for uniform analysis.

The ΔΔCt method (Life Technologies, see also Livak K J, Schmittgen T D, Analysis of relative gene expression data using real-time quantitative PCR and the 2(−ΔΔ C(T)) Method. Methods. (2001) December; 25(4):402-8) was used for analysis, with the geometric mean of both hsa-miR-106a and ath-159a used as endogenous control, and the average relative Ct values of NC patients being used to calibrate all the individual values. Linear fold changes were then calculated and plotted on scatter plots using Prism (GraphPad Prism Software, San Diego, Calif.-USA). (Note: signature validation for Cohort 2 (see Example 2) was done exactly as described above, but the RT and pre-amplification primer pools were prepared using only the signature and normalization control specific primers (miR-301a, miR-191, miR-15b, let-7g, let-7d, miR-545, miR-142-3p, miR-106a and ath-159a). miRNA-specific primers and probes were purchased from Applied Biosystems, under Cat. Nos. 000464 (miR-142-3p), 001289 (miR-545), 000380 (let-7d), 000490 (miR-191), 000528 (miR-301a), 000383 (let-7g), 000390 (miR-15b), 000578 (miR-106a), and 000338 (ath-159a)).

Example 2: Signature Generation and Predictive Model Building

The miRNAs identified and validated as having significantly different expression between AD and NC samples in Cohort 1 (fold change>1.5, p value<0.005) were selected for predictive model building. The expression values of 7 miRNAs (let-7d, miR-191, miR-301a, miR-545, let-7g, miR-15b, miR-142-3p) from each of the AD (n=11) and NC (n=20) samples in Cohort 1 were used as input for a signature building model. In particular, the relative Ct values (observed Ct values of individual miRNAs minus the geometric mean of Ath-159a and miR-106a Ct values) for each of the 7 miRNAs obtained from Taqman qPCR of Cohort 1 samples were used to build a linear classifier to separate AD from NC samples (relative Ct values are shown in Table 4). All possible non-zero subsets of the 7 miRNAs (127 signatures) were used for linear discriminatory analysis (LDA). For LDA, the MASS software package was used in the windows implementation of R version 2.12.2 (Venables, W. N. & Ripley, B. D. (2002) Modern Applied Statistics with S. Fourth Edition. Springer, New York. ISBN 0-387-95457-0). The source code of the package is available at: http://cran.r-project.org/web/packages/MASS/index.html. Other suitable software packages can be used or developed. Area-under-curve (AUC) numbers were also calculated in R (version 2.12.2) using the software package "verification" (source code available at http://cran.r-project.org/web/packages/verification/index.html; see also Mason, S. J. and N. E. Graham. "Areas beneath the relative operating characteristics (ROC) and relative operating levels (ROL) curves: Statistical significance and interpretation," Q. J. R. Meteorol. Soc. 30 (1982) 291-303). Other suitable software packages can be used or developed.

A sample code and description of the input files used to calculate the prediction accuracy, sensitivity, specificity and AUC numbers is set forth below. This code shows how to classify unknown samples as AD or Normal using a representative signature of three miRNAs ("miR-545", "let-7g", "miR-15b"). The code for performing a classification based on any combination of the 7 validated miRNAs would be similar, and it should be understood that signatures based on any combination of these 7 miRNAs may be used. For any combination or for an individual miRNA selected from the 7 validated miRNAs we can build a linear discriminant model by determining the coefficients of the LDA model based on the training data obtained from Cohort 1. Once we have determined the model based on Cohort 1 we can predict for any new sample if the individual from whom the sample was obtained is an AD individual, or a normal individual. In order to make a prediction for a new sample we need to determine the miRNA expression levels for each individual miRNA in the signature. Based on these values, the model will return the ("posteriori") probability that the new sample is from an individual having AD. The cut-off value of this probability determines the sensitivity and specificity of the model. For our predictions we determined accuracy, sensitivity and specificity at a threshold of 0.5 (that is, if the probability of a sample being AD is larger than 0.5, our model classified it as AD).

Exemplary input files may be in the form of train.txt, validation.txt, train_an.txt and validation_an.txt. "Train.txt" is the file which contains the expression profile for Cohort 1 in a form of a matrix, where the rows are the samples and the columns are the miRNAs. The first row contains the names of the miRNAs and the first column the names of the samples. The "train_an.txt" file contains the annotation of the samples. There are two columns, where the first column contains the name of the sample and the second column the annotation of the samples ("normal" and "AD" in this case). The files "validation.txt" and "validation_an.txt" contains the data and annotation for Cohort 2 in exactly the same format. The variables prediction$class and prediction$posteri contains the predicted annotation and the corresponding probability of the samples from Cohort 2.

Exemplary code which may be used to calculate the prediction accuracy, sensitivity, specificity and AUC numbers is as follows:

```
read.file <- function(file,inv)
{
data.tmp=read.csv(file,sep="\t",header=T)
mat <- matrix(0, nrow=nrow(data.tmp), ncol=ncol((data.tmp))-1)
rownames(mat)=data.tmp[,1]
colnames(mat)=colnames(data.tmp)[2:ncol(data.tmp)]
for(i in 1:nrow(data.tmp))
{
mat[i,]=as.numeric(data.tmp[i,2:ncol(data.tmp)])
}
if(inv==T) {mat=t(mat) }
mat
}
library(MASS)
library(verification)
train=read.file("train.txt",F)
validation=read.file("validation.txt",F)
train_an=read.table("train_an.txt")
validation_an=read.table("validation_an.txt")
validation_an=as.factor(validation_an[,1])
train_an=as.factor(train_an[,1])
obs=NULL
obs[validation_an=="normal"]=0
obs[validation_an=="AD"]=1
set=c("miR.545","let.7g","miR.15b")
train_sp=train[,set]
ldatrain=lda((train_sp),train_an)
validation_sp=validation[,set]
prediction= predict(ldatrain,validation_sp)
tb=table(validation_an,prediction$class)
nr=tb[1,1]+tb[2,2]
accuracy=nr/sum(tb)
sensitivity=tb[1,1]/(tb[1,1]+tb[1,2])
specificity=tb[2,2]/(tb[2,1]+tb[2,2])
auc=roc.area(obs,prediction$posteri[,1])$A
```

To perform a classification based on any combination of the 7 validated miRNAs, sample code similar to that shown above may be used. Alternatively, other software code useful for prediction, or for calculating prediction accuracy, sensitivity, specificity and AUC from a data set may be used in place of the sample code described above.

Example 3: miRNA Biomarkers Predict the Status of Subjects as Normal or as Having Alzheimer's Disease The performance of a predictive model using all non-zero subsets of the 7 validated miRNAs (let-7d, let-7g, miR-15b, miR-142-3p, miR-191, miR-301a and miR-545) as described in Example 2 was evaluated based on the classification results of human plasma samples from a second cohort containing 20 AD and 17 NC patients ("Cohort 2") obtained from PrecisionMed, Inc. Age, sex, diagnosis, and MMSE scores for patients in Cohort 2 are provided in Table 5. The performance of the predictive model was evaluated based on accuracy, specificity, sensitivity and area under curve (AUC) numbers.

Total RNA extraction was carried out using only 500 μl of plasma from each Cohort 2 sample as described in Example 1, followed by TaqMan RT-qPCR analysis. We achieved significant correlation with average fold changes between the two cohorts for the signature miRNAs being very closely replicated, and with excellent p-values (FIG. 3, Table 6).

The relative Ct values (observed Ct values of individual miRNAs minus the geometric mean of Ath-159a and miR-106a Ct values) for each of the candidate miRNAs (let-7d, let-7g, miR-15b, miR-142-3p, miR-191, miR-301a and miR-545) from each of the Cohort 2 samples were then used as input (Table 7) for the signature miRNA prediction algorithm, which was developed based on Cohort 1 data as described above. All potential signatures are listed in Table 8. Signatures with >75% accuracy are shown in Table 9, while signatures with >89% accuracy are shown in Table 10. The over-all signature accuracy was calculated as the fraction of misclassified samples (AD or NC). The sensitivity characterizes the predictive models' ability to identify true positives, which in this study was calculated as the number of correctly identified AD samples divided by the total number of AD samples. On the other hand, the specificity was the number of correctly classified NC samples (true negatives) divided by the total number of NC samples. The AUC was calculated as the area under the receiver operating characteristic (ROC) curve, which is a plot of the sensitivity vs. the false positive rate (1-specificity). The ROC curve was generated by varying the threshold for the prediction probability.

The combination of miR-545, let-7g and miR-15b resulted in the highest specificity (94.1%), sensitivity (95%) and AUC (0.953). Signature combinations ranged from just two miRNAs (e.g. miR-15b and miR-545) up to 7 miRNAs (e.g. miR-191, miR-301a, miR-545, let-7g, let-7d, miR-15b and miR-142-3p) (see Table 8A-8C). Each signature had different combinations of the candidate miRNA biomarkers and resulted in varying specificity and sensitivity (see Table 9A-9B). In addition, we also examined the signature accuracy for individual miRNAs (Table 11). The signature accuracy was lower for individual miRNAs in comparison to combination signatures. The best stand-alone miRNAs in terms of specificity were miR-142-3p and miR-301a, with both having 100% specificity. But miR-142-3p had better sensitivity (65%) as compared to 25% sensitivity for miR-301a. Let-7g and miR-191 had the best sensitivity at 95%, but only miR-191 had enriched specificity of 76%. miR-191, miR-15b and let-7d had the best overall accuracy of the stand-alone miRNAs.

---

What is claimed is:

1. A method of detecting the level of one or more miRNAs in a plasma or serum sample from a subject known or suspected of having cognitive impairment due to Alzheimer's Disease or Mild Cognitive Impairment (MCI), said method comprising:
providing a plasma or serum sample from the subject known or suspected of having cognitive impairment due to Alzheimer's Disease or MCI; and
detecting the level of at least one miRNA selected from the group consisting of miR-191, miR-15b, miR-142-3p, Let-7g, Let-7d, and combinations thereof, in the plasma or serum sample by contacting the plasma or serum sample with an agent that specifically hybridizes to the at least one miRNA, or a cDNA derived therefrom, and detecting the level of hybridization between the agent and the at least one miRNA, or cDNA derived therefrom.

2. The method of claim 1, comprising detecting the level of one miRNA selected from the group consisting of miR-191, miR-15b, miR-142-3p, Let-7g, and Let-7d in the plasma or serum sample.

3. The method of claim 1, further comprising detecting the level of at least one additional miRNA in the plasma or serum sample selected from the group consisting of miR-301a; miR-545; and miR-301a and miR-545.

4. The method of claim 3, comprising detecting the level of at least two miRNAs in the sample.

5. The method of claim 3, comprising detecting the level of miR-545, let-7g, and miR-15b.

6. The method of claim 3, comprising detecting the level of miR-15b and miR-545.

7. The method of claim 3, comprising detecting the level of miR-301a, miR-545, let-7g and miR-15b.

8. The method of claim 3, comprising detecting the level of miR-191, miR-301a, and miR-545.

9. The method of claim 3, comprising detecting the level of miR-301a, let-7g, and miR-15b.

10. The method of claim 3, comprising detecting the level of miR-191, miR-301a, miR-545, and miR-15b.

11. The method of claim 3, comprising detecting the level of at least three miRNAs selected from the group consisting of miR-191, miR-15b, miR-142-3p, Let-7g, Let-7d, miR-301a, and miR-545, in the plasma or serum sample.

12. The method of claim 1, comprising detecting the level of at least two miRNAs in the sample, wherein said miRNAs are selected from the group consisting of miR-191, miR-15b, miR-142-3p, Let-7g, Let-7d, and combinations thereof.

13. The method of claim 1, comprising detecting the level of miR-191 and miR-15b.

14. The method of claim 1, comprising detecting the level of Let-7g and miR-15b.

15. The method of claim 1, wherein the plasma or serum sample is a microvesicle-free sample.

16. The method of claim 1, wherein the sample is plasma.

17. The method of claim 1, wherein the sample is serum.

18. The method of claim 1, wherein the subject known or suspected of having cognitive impairment due to Alzheimer's Disease or MCI is selected based on performance in a cognitive test to facilitate diagnosis of Alzheimer's Disease.

19. The method of claim 18, wherein the cognitive test is selected from the group consisting of the mini-mental state examination (MMSE), mini-cog test, ADAS-cog test, and clock-drawing test.

20. The method of claim 1, further comprising administering to the subject a therapeutically effective amount of a pharmaceutical composition comprising an Alzheimer's therapeutic or a pharmaceutically acceptable salt or ester thereof.

21. The method of claim 20, wherein the Alzheimer's therapeutic is selected from the group consisting of galantamine, rivastigmine and donepezil.

22. The method of claim 1, wherein the agent that specifically hybridizes to the miRNA is a nucleic acid molecule.

23. The method of claim 1, wherein the level of hybridization between the agent and the at least one miRNA is detected using amplification, hybridization, and/or sequencing methods.

24. The method of claim 23, wherein the level of hybridization between the agent and the at least one miRNA is detected using polymerase chain reaction (PCR), Real-Time PCR (RT-PCR), quantitative PCR (qPCR), or rolling circle amplification.

25. The method of claim 23, wherein the level of hybridization between the agent and a the at least one miRNA is detected using microarray, NanoString nCounter analysis, Northern blot, branched DNA signal amplification, or in situ hybridization.

26. The method of claim 23, wherein the level of hybridization between the agent and the at least one miRNA is detected using next-generation sequencing.

27. The method of claim 1, wherein the subject is a mammal.

28. The method of claim 1, wherein the subject is human.

29. A method of detecting the level of one or more miRNAs in a plasma or serum sample from a subject having cognitive impairment with an MMSE score of 0-26, comprising:
providing a plasma or serum sample from the subject having cognitive impairment; and
detecting the level of at least one miRNA selected from the group consisting of miR-191, miR-15b, miR-142-3p, Let-7g, Let-7d, and combinations thereof, in the plasma or serum sample by contacting the plasma or serum sample with an agent that specifically hybridizes to the at least one miRNA, or a cDNA derived therefrom, and detecting the level of hybridization between the agent and the at least one miRNA, or cDNA derived therefrom.

30. The method of claim 29, further comprising detecting the level of at least one additional miRNA in the plasma or serum sample selected from the group consisting of miR-301a; miR-545; and miR-301a and miR-545.

31. A method of detecting the level of one or more miRNAs in a plasma or serum sample from a subject having cognitive impairment with an MMSE score of 21-26, comprising:
providing a plasma or serum sample from the subject having cognitive impairment; and
detecting the level of at least one miRNA selected from the group consisting of miR-191, miR-15b, miR-142-3p, Let-7g, Let-7d, and combinations thereof, in the plasma or serum sample by contacting the plasma or serum sample with an agent that specifically hybridizes to the at least one miRNA, or a cDNA derived therefrom, and detecting the level of hybridization between the agent and the at least one miRNA, or cDNA derived therefrom.

32. The method of claim 31, further comprising detecting the level of at least one additional miRNA in the plasma or serum sample selected from the group consisting of miR-301a; miR-545; and miR-301a and miR-545.

33. A method of detecting the level of one or more miRNAs in a subject known or suspected of having cognitive impairment due to Alzheimer's Disease or Mild Cognitive Impairment (MCI), said method comprising:
providing a plasma or serum sample from the subject known or suspected of having cognitive impairment due to Alzheimer's Disease or MCI; and
detecting the level of at least one miRNA selected from the group consisting of miR-191, miR-15b, miR-142-3p, Let-7g, Let-7d, and combinations thereof, in the plasma or serum sample, by contacting the plasma or serum sample with a nucleic acid molecule that specifically hybridizes to the at least one miRNA, or a cDNA derived therefrom, wherein the nucleic acid molecule comprises a sequence complementary to all or a portion of SEQ ID NO:2, SEQ ID NO:4, SEQ ID NO:5, SEQ ID NO:7, or SEQ ID NO:8, and detecting the level of hybridization between the nucleic acid molecule and the at least one miRNA, or cDNA derived therefrom.

34. The method of claim 33, further comprising detecting the level of at least one additional miRNA in the sample selected from the group consisting of miR-301a; miR-545; and miR-301a and miR-545.

35. The method of claim 33, comprising detecting the level of at least three miRNAs selected from the group consisting of miR-191, miR-15b, miR-142-3p, Let-7g, Let-7d, miR-301a, and miR-545.

36. The method of claim 33, comprising detecting the level of at least two miRNAs selected from the group consisting of:
   (a) miR-545, let7g, and miR-15b,
   (b) miR-15b and miR-545,
   (c) miR-301a, miR-545, let-7g and miR-15b,
   (d) miR-191 and miR-15b,
   (e) Let-7g and miR-15b,
   (f) miR-191, miR-301a, and miR-545,
   (g) miR-301a, let-7g, and miR-15b, and
   (h) miR-191, miR-301a, miR-545, and miR-15b.

37. The method of claim 33, wherein the level of hybridization between the nucleic acid molecule and the at least one miRNA is detected using amplification, hybridization, and/or sequencing methods.

* * * * *